US009468406B2

(12) United States Patent
Dieckmann et al.

(10) Patent No.: US 9,468,406 B2
(45) Date of Patent: Oct. 18, 2016

(54) DOSIMETER SYSTEM

(71) Applicant: EUROPEAN SPACE AGENCY, Paris (FR)

(72) Inventors: Matthias Dieckmann, The Hague (NL); Ulrich Straube, Bonn (DE); Thomas Berger, Köln (DE); Marlies Luszik-Bhadra, Braunschweig (DE)

(73) Assignee: EUROPEAN SPACE AGENCY, Paris (FR)

( * ) Notice: Subject to any disclaimer, the term of this patent is extended or adjusted under 35 U.S.C. 154(b) by 0 days.

(21) Appl. No.: 14/913,511

(22) PCT Filed: Aug. 20, 2013

(86) PCT No.: PCT/EP2013/067307
§ 371 (c)(1),
(2) Date: Feb. 22, 2016

(87) PCT Pub. No.: WO2015/024591
PCT Pub. Date: Feb. 26, 2015

(65) Prior Publication Data
US 2016/0198999 A1 Jul. 14, 2016

(51) Int. Cl.
*G01T 1/02* (2006.01)
*A61B 5/00* (2006.01)
*G01T 1/185* (2006.01)

(52) U.S. Cl.
CPC ............ *A61B 5/4845* (2013.01); *G01T 1/026* (2013.01); *G01T 1/185* (2013.01)

(58) Field of Classification Search
CPC .................... G01T 1/02; G01T 1/026
See application file for complete search history.

(56) References Cited

U.S. PATENT DOCUMENTS

| 3,678,275 A | 7/1972 | Schneider et al. |
| 2002/0180606 A1 | 12/2002 | Kitaguchi et al. |
| 2010/0065749 A1* | 3/2010 | Nomura ............... A61N 5/1048 250/389 |

FOREIGN PATENT DOCUMENTS

| JP | 2007-285914 A | 11/2007 |
| WO | 2005/008286 A2 | 1/2005 |

OTHER PUBLICATIONS

Feb. 23, 2016 International Preliminary Report on Patentability issued in International Patent Application No. PCT/EP2013/067307.

(Continued)

*Primary Examiner* — Marcus Taningco
(74) *Attorney, Agent, or Firm* — Oliff PLC

(57) ABSTRACT

A dosimeter system for determining radiation exposure including first and second units, where the first unit determines a first quantity indicating influence of a first radiation field, and transmitting the first quantity by the first detecting-unit to the second unit, where the second unit determines second quantity indicative of influence of a second radiation field on biological tissue, third detecting-unit determines a third quantity indicative of an influence of the second radiation field, where the third detecting-unit is of the same type as the first detecting-unit included by the first unit, and determining quantity for adjusting the first quantity on basis of the second quantity by the second detecting-unit and third quantity by the third detecting-unit, adjusting the first quantity so a fourth quantity indicative of an influence of the first radiation field on biological tissue based on the first quantity by the first detecting-unit and adjusting the first quantity.

16 Claims, 8 Drawing Sheets

(56) References Cited

OTHER PUBLICATIONS

Jul. 28, 2014 Search Report issued in International Patent Application No. PCT/EP2013/067307.
Jul. 28, 2014 Written Opinion issued in International Patent Application No. PCT/EP2013/067307.
Luszik-Bhadra, M. et al., "Response calculations for silicon-based direct-reading dosimeters for use at the International space station (ISS)," Elsevier, Radiation Measurements, vol. 45, (2010), pp. 1548-1552.
Akatov, Y. et al., "Dosimetric complex for long-term manned space flights," International Journal of Radiation Applications and Instrumentation, Part D., Nuclear Tracks and Radiation Measurements, vol. 20, No. 1, pp. 7-11, 1992).
Booz, J., "Advantages of Introducing Microdosimetric Instruments and Methods into Radiation Protection," Radiation Protection Dosimetry, vol. 9, No. 3, pp. 175-183, (1984).
Apathy, I. et al., "Personal Dosimetry for Human Missions to Mars Based on TLD and Let-Spectrometry Technique," Adv. Space Res. vol. 31, No. 1, pp. 39-44, (2003).
Moro, D. et al., "EuTEPC—(European Tissue Equivalent Proportional Counter): a Microdosimeter for the Assessment of the Radiation Quality at the International Space Station," Jan. 1, 2012, Retrieved from the Internet: URL:http://www.Inl.infn.it/~annrep/read_ar/2011/contributions/pdfs/111_B_83_B078.pdf, retrieved on May 8, 2014.
Hayashi, Takayoshi et al., "Measurement of Let Distribution and Dose Equivalent on Board the Space Shuttle STS-65," Radiation Measurements, vol. 26, No. 6, pp. 935-945, (1996).

* cited by examiner

DOSIMETER SYSTEM

TECHNICAL FIELD OF THE INVENTION

The present invention relates to a dosimeter system for determining a radiation exposure e.g. of persons moving in an environment where ionizing radiation is present (radiation environment).

The invention is particularly though not exclusively developed and applicable to the medical monitoring radiation exposure of humans in space (e.g. astronauts, cosmonauts, taikonauts etc.), crew within human spaceflight, i.e. crew members of spacecraft and earth orbiting space stations. It may be used for aircrew personnel or personnel of nuclear power plants, and workers involved in rescue and cleanup operations during or after nuclear accidents.

BACKGROUND OF THE INVENTION

In the art, radiation exposure of persons moving in a radiation environment is determined by means of a mobile dosimeter carried by the respective person. An absorbed dose measured by the mobile dosimeter in units of Gray (1 Gy=1 J/kg) is translated into the dose equivalent which has been designed to represent the stochastic biological effects of ionizing radiation on human tissue and which is measured in units of Sievert (1 Sv=1 J/kg)). This translation between absorbed dose and dose equivalent is performed on the basis of Linear Energy Transfer (LET) dependent quality factors (Q factors). Accordingly, having accurate knowledge of the deposited energy of particles in the mobile dosimeter is of key importance in determining the dose equivalent, which alone allows assessing the physiological impact of the radiation.

However, radiation fields may significantly vary, particularly in space, with regard to aspects such as their particle content, energy spectrum of particles, intensity of particle flux, and the like. Accordingly, mobile dosimeters are typically adapted for specific use in a given type of radiation environment. If the kind of particles present in the radiation environment is known (e.g. predominantly alpha particles, predominantly protons, predominantly electrons, predominantly neutrons or predominantly gamma rays, or known compositions of any of the aforementioned), and also the typical energy distribution and particle flux is known, the mobile dosimeter can be calibrated to perform optimally in the respective known radiation environment. Rather accurate knowledge of the expected radiation environment is typically the case e.g. in nuclear power plants during normal operation or in laboratories in which medical equipment such as an x-ray apparatus is operated.

On the other hand, due to their specific calibration, mobile dosimeters may yield inaccurate results if the actual radiation environment deviates from the expected radiation environment for which the mobile dosimeter had been calibrated. As a result, a determined dose equivalent may deviate from the actual dose equivalent received by the person carrying the mobile dosimeter. For astronaut health monitoring as well as for any occupational health and safety monitoring, self-evidently, this situation is undesirable and has to be corrected to minimal acceptable limits.

Therefore, an accurate knowledge of the actual characteristics of the radiation environment is of key importance. Most known mobile dosimeters for ionizing radiation however are passive dosimeters and need offline analysis for determining the so-called side variables related to characteristics of the radiation environment. In these mobile dosimeters, a possible deviation between the expected radiation environment and the actual radiation environment can only be determined after exposure and post processing (i.e. on ground as regards human spaceflight).

Active dosimeters known in the art on the other hand do also not provide side variables online, so that there is a possibility that a mismatch between the specific calibration of the dosimeter and an optimal calibration for the actual radiation field may not be immediately detected. Hence, the accuracy of the dosimeter may be reduced, which may be only recognizable after exposure and post processing.

Accordingly, using conventional dosimeters in a radiation environment that is either not known to begin with, or that may change over time, there is a risk that harmful radiation is overlooked and that moreover the dose equivalent received by the relevant person under surveillance is not determined correctly by the mobile dosimeter.

Such a radiation environment in which conventional mobile dosimeters are expected to fail is present e.g. in space stations orbiting earth at a low earth orbit (LEO), and also generally in space. The radiation field in low earth orbit is known to be the most complex natural radiation environment encountered by humans. A further environment in which conventional mobile dosimeters are expected to fail may be present on a site of a nuclear accident, such as the recent Fukushima accident.

The radiation environments mentioned above may also vary with regard to their characteristics with position, and can change with time, which triggers another challenge to conventional mobile dosimeters.

SUMMARY OF THE INVENTION

In order to monitor and adequately protect personnel operating in a radiation environment, in particular humans in space (e.g. astronauts, cosmonauts, taikonauts etc.) and other professionals, from receiving dose equivalents of radiation beyond accepted limits and to execute the mutually acknowledged ALARA principle (As Low As Reasonably Achievable, the internationally accepted basic paradigm applicable in radiation protection), it is deemed necessary to have available a dosimeter system that is able to determine a dose equivalent accurately and in real time, regardless of a particular nature of the radiation environment.

It is thus an object of the present invention to overcome the limitations of the prior art discussed above. It is another object of the invention to provide a dosimeter system capable of determining a dose equivalent accurately, regardless of a particular nature of radiation environment. It is another object of the invention to provide a dosimeter system capable of determining a dose equivalent in real time. It is yet another object of the invention to provide an active personal dosimeter capable of determining an accurate dose equivalent in real time.

In view of at least some of the above objects, the present invention proposes a dosimeter system, a method for determining radiation exposure and a mobile unit of a dosimeter system having the features of the respective independent claims. Preferred embodiments of the invention are described in the dependent claims.

According to a preferred embodiment of the present invention, a dosimeter system for determining radiation exposure includes a first unit and a second unit, wherein the first unit comprises first detecting means configured for determining a first quantity indicative of an influence of a first radiation field, and transmitting means for transmitting the first quantity determined by the first detecting means to the second unit, wherein the second unit comprises second detecting means configured for determining a second quantity indicative of an influence of a second radiation field on biological tissue, third detecting means configured for determining a third quantity indicative of an influence of the second radiation field, wherein the third detecting means is of the same type as the first detecting means comprised by the first unit, and means for determining a quantity for adjusting the first quantity on the basis of the second quantity determined by the second detecting means and the third quantity determined by the third detecting means, wherein the quantity for adjusting the first quantity is determined such that a fourth quantity indicative of an influence of the first radiation field on biological tissue can be determined on the basis of the first quantity determined by the first detecting means and the quantity for adjusting the first quantity. Preferably, the biological tissue is human tissue. Preferably, the quantity for adjusting the first quantity is determined in real time.

Preferably, the second unit further comprises means for determining the fourth quantity indicative of an influence of the first radiation field on biological tissue on the basis of the first quantity determined by the first detecting means and the quantity for adjusting the first quantity. If the fourth quantity exceeds a predetermined threshold for the fourth quantity, an alarm and/or a warning message may be issued.

By providing a main unit (second unit) that has, in addition to the third detecting means, also a dedicated detector capable of measuring a dose equivalent (second detecting means), suitability of a calibration of a first detecting means of a mobile dosimeter unit (first unit) can be tested on the basis of data gathered by the main unit. A dose equivalent determined either by the mobile dosimeter unit or on the basis of data gathered by the mobile dosimeter unit can be corrected appropriately if the calibration of the first detecting means turns out to be not suited to the present radiation environment. This is achieved by determining an appropriate adjustment term (quantity for adjusting the first quantity) and adjusting the first quantity in accordance with the adjustment term. Herein, appropriateness of the adjustment term is ensured by taking into account an output of the third detecting means which is of the same type as the first detecting means, and an output (i.e. a dose equivalent) of the dedicated detector.

The accurate knowledge of an influence of the first radiation field on biological (e.g. human) tissue in real time offers the possibility to deduce the influence of the first radiation field on complex biological systems, including the human body, accurately and in real time. This deduction may be performed on the basis of predetermined (e.g. table-stored) coefficients that relate the influence of the first radiation field on the biological tissue to an influence of the first radiation field on specific tissue comprised by the biological system under consideration. For instance, plural coefficients each relating to a different organ of the human body can be used to determine the influence on the respective organs. Doing so, an overall influence of the radiation on the human body can be calculated from the known influence of the first radiation field on biological tissue. Accordingly, a respective person under surveillance can be notified in real time of the health-related consequences of his present radiation exposure. This poses a significant advantage over the prior art, in which such information was only available to the person under surveillance after exposure and post processing, or—if delivered event-related and simultaneously—without real-time derived and updated calibration data, hence affected by errors.

Since the main unit and the mobile dosimeter unit respectively comprise detecting means that are of the same type (first and third detecting means), the testing of the calibration of the first detecting means on the basis of data gathered by the main unit is also not affected by systematic uncertainties. Likewise, aging and deterioration effects of the first detecting means—both of the actual detecting device and any circuitry connected thereto—are automatically taken into account by the inventive setup. Accordingly, unlike in the conventional art accuracy of the dose equivalent that is determined by the inventive dosimeter system on the basis of a first quantity determined by the first detecting means of the mobile dosimeter unit is not affected by aging and deterioration effects. In consequence, the present invention is capable of providing highly accurate dose equivalents received by a relevant person under surveillance by the mobile dosimeter unit, regardless of the nature of the radiation environment (first radiation field), i.e. regardless of a particle composition of the radiation environment, an energy spectrum of the respective particles and an intensity or flux of particles in the radiation environment, and also regardless of a duration for which the mobile dosimeter unit has been used (i.e. the age of the mobile dosimeter unit).

Since the first quantity determined in the mobile unit is transmitted to the main unit, the actual dose equivalent received by the carrier of the mobile dosimeter unit can be determined not only in the mobile dosimeter unit, but also in the main unit in real time. Thus, appropriate measures can be taken to avoid over-exposure of the relevant person under surveillance. For instance, if it is found that the dose equivalent received by the relevant person under surveillance approaches a critical limit, he can be warned and/or ordered to leave an area in which strong radiation is present, or to proceed to a radiation shelter. This presents a clear advantage compared to conventional passive dosimeters, for which an accurate measure of the dose equivalent is only available after the dosimeter has been read out dosimeter and side variables related to characteristics of the radiation environment have been determined, so that a timely (proactive) warning on the basis of an accurately determined dose equivalent would not be possible under all circumstances.

It is particularly advantageous if the main unit comprises not only a detecting device that is of the same type as the detecting device of the mobile dosimeter unit, but instead comprises a complete further mobile dosimeter unit. Thereby, not only further systematic errors can be excluded, but it also becomes possible to simplify the internal structure of the main unit, and to replace, if needs be, the third detecting means (comprised by the further mobile dosimeter) in the main unit that is of the same type as the one in the mobile dosimeter unit.

By this measure, systematic errors in testing the calibration of the mobile dosimeter unit and in determining the dose equivalent can be excluded almost entirely.

Preferably, the first quantity is a quantity indicative of an influence of the first radiation field on biological tissue and the third quantity is a quantity indicative of an influence of the second radiation field on biological tissue. Further preferably, the first quantity is a dose equivalent and the third quantity is a dose equivalent.

In this case, the first quantity that is determined by the first detecting means of the mobile dosimeter unit and transmitted to the main unit can be very easily adjusted e.g. by addition of an adjustment term obtained by comparing the output (dose equivalent) determined by the dedicated detector (second detecting means) of the main unit and the output of the third detecting means of the main unit, or by multiplication by such an adjustment term.

In addition, the first unit may further comprise means for determining a position of the first unit, the transmitting means may be configured to transmit the first quantity determined by the first detecting means and the determined position of the first unit to the second unit, and the second unit may comprise means for determining a function indicative of an intensity of the first radiation field in dependence on the position of the first unit, on the basis of the first quantity and the determined position of the first unit.

A particular advantage is achieved if the system comprises a plurality of first units and the second unit comprises means for determining a spatial distribution of the first radiation field in which the plurality of first units are present on the basis of the respective functions indicative of the intensity of the first radiation field in dependence on the position of the respective first unit.

By providing the mobile dosimeter unit with means for determining the position of the mobile dosimeter unit, such as a Global Navigation Satellite System (GNSS) receiver, e.g. a GPS receiver or a Galileo receiver, and by transmitting the determined position together with the determined first quantity to the main unit, the main unit is enabled to record a trajectory in space along which the mobile dosimeter unit is moved together with a value that is representative of the radiation present at the respective point in space. As data accumulates in the main unit, this data can be used to determine a spatial distribution of the radiation field, which can be used for planning future operations within the radiation field. For instance, if a spatial distribution of a radiation field at certain timing within a space station is known in advance, this information can be used to determine an allowable duration of presence of a crew member at a given location in the space station or to determine a work program that avoids areas with high levels of radiation.

In case the dosimeter system comprises more than one mobile dosimeter unit, data that can be used for determining a spatial distribution of the radiation field accumulates more quickly. Moreover, in this case a zone in which radiation is particularly strong can be determined in real time on the basis of the output of one of the mobile dosimeter units that happens to be present in the respective zone, and the carriers of the further mobile dosimeter units (persons under surveillance) can be warned on short notice to not enter said zone. Such early warning of carriers of the mobile dosimeter units is particularly useful when performing rescue and cleanup operations during or after a nuclear accident.

It is preferred that the first detecting means comprises a first detecting device configured for detecting a first variable related to an ionizing particle incident on the first detecting device, and the first detecting device has a first range in which the first variable can be detected. Therein, the first variable preferably is a deposited energy (an energy deposited in the first detecting device by an ionizing particle) or a linear energy transfer (an energy transferred to the first detecting device by an ionizing particle per unit path length). It is further preferred that the first detecting means further comprises a second detecting device configured for detecting a second variable related to an ionizing particle incident on the second detecting device, the second detecting device has a second range in which the second variable can be detected, and the first detecting means is configured to obtain the first quantity on the basis of an output of the first and second detecting devices. Therein, the second variable preferably is a deposited energy or a linear energy transfer. It is further preferred that the first and second detecting devices are configured so that a range obtained by combining the first and second ranges consists of a first sub-range covered by the first detecting device only, a second sub-range covered by the second detecting device only, and a third sub-range covered by both the first and second detecting devices. It is yet further preferred that the first detecting means further comprises a third detecting device configured for detecting a third variable related to an ionizing particle incident on the third detecting device, the third detecting device has a third range in which the third variable can be detected, the range obtained by combining the first and second ranges is fully contained in the third range, and the first detecting means is configured to obtain the first quantity on the basis of an output of the first, second and third detecting devices. Therein, the third variable preferably is a deposited energy or linear energy transfer. Preferably, the third detecting device is of a different type as the first and second detecting devices, which preferably are of the same type.

Providing first and second detecting devices that have different ranges in which an energy variable (e.g. a deposited energy or a linear energy transfer to the respective detecting device) can be detected allows maintaining sufficient detection accuracy over the whole combined range. Both the first and second detecting devices can be specifically adapted to their respective ranges, e.g. with respect to their physical dimensions and operation parameters. However, for measurements relating to combined ranges there typically is the need to apply different quality factors to the outputs of the individual detecting devices, and to take into account corrections for a double-counted range that is covered by both the detecting devices. Moreover, it is desirable to be able to check a calibration of the first and second detecting devices already at this stage.

In order to deal with these issues, the present invention also provides a third detecting device that has a range in which the third variable (e.g. a deposited energy or a linear energy transfer) can be detected and which fully contains the combined range. While the output of this third detecting device may be inferior to the outputs of the first and second detecting devices as regards accuracy, it provides a valuable means for cross-checking the combined output of the first and second detecting devices. By comparing an absorbed dose obtained on the basis of the outputs of the first and second detecting devices to an absorbed dose obtained on the basis of an output of the third detecting device, a plausibility of the former absorbed dose (and of the underlying output of the first and second detecting devices) can be assessed. If the respective absorbed doses deviate by more than a predetermined margin, a warning message may be issued, whereas if the respective absorbed doses agree with each other within the predetermined margin, the outputs of the first and second detecting devices can be used as a basis for determining a dose equivalent as the first quantity.

The first detecting means may further comprise a fourth detecting device configured for detecting a time-integrated value of a fourth variable related to an ionizing particle incident on the fourth detecting device. Preferably, the fourth variable is an energy deposited in the fourth detecting device, and the fourth detecting device is configured for detecting a total energy that is deposited in the fourth detecting device by ionizing particles incident on the fourth detecting device over time.

Such a detecting device typically is not comparable to detecting devices capable of resolving single events of energy deposition with regard to sensitivity and accuracy. On the other hand, the fourth detecting device provides for a reliable detection of very high absorbed doses even at a very high level of radiation, e.g. during radiation bursts (high dose events). Therefore, the fourth detecting device provides for a reliable warning system that may issue an alert to the relevant person under surveillance, and/or to the main unit, even in a case in which the first through third detecting means fail to provide a viable (i.e. an accurate) output due to a very high level of radiation.

It is of particular advantage if the first unit comprises a shock detector configured for detecting a mechanic shock of the first unit, and means for correcting the first quantity determined by the first detecting means for an influence of the mechanic shock of the first unit detected by the shock detector.

Oftentimes, mechanical shock of a mobile dosimeter unit results in a spurious output of the detecting means which is not due to actual radiation. By virtue of the above feature, such spurious outputs, which would result in incorrectly measured absorbed doses and dose equivalents, can be effectively corrected for.

It is further preferred that the second unit comprises mounting means configured for receiving the first unit in the mounting means, for charging a battery of the first unit and/or for read or write operations to or from a memory of the first unit.

Providing mounting means such as a slot for receiving the mobile dosimeter unit allows for particularly convenient and simple recharging of a battery of the mobile dosimeter, reading out data from a memory of the mobile dosimeter, and writing data to the memory of the mobile dosimeter. Thereby, e.g. a calibration scheme stored in the memory of the mobile dosimeter unit can be adjusted on a regular basis while the battery of the mobile dosimeter unit is being recharged.

The transmitting means may be configured to transmit the first quantity determined by the first detecting means to the second unit through a wireless connection, and/or to transmit the first quantity determined by the first detecting means to the second unit at predetermined time intervals, i.e. with predetermined periodicity. Preferably, the first through third quantities correspond to a predetermined period of time, and the time interval for transmission matches the predetermined period of time.

Further, the second unit may comprise transmitting means configured for transmitting data comprising at least one of the first quantity determined by the first detecting means, the second quantity, the third quantity and the fourth quantity to a third unit which is configured to analyze the received data.

According to a further preferred embodiment of the present invention, a method for determining radiation exposure comprises determining a first quantity indicative of an influence of a first radiation field by a first detecting means, determining a second quantity indicative of an influence of a second radiation field on biological tissue by a second detecting means, determining a third quantity indicative of an influence of the second radiation field by a third detecting means, wherein the third detecting means is of the same type as the first detecting means, determining a quantity for adjusting the first quantity on the basis of the second quantity determined by the second detecting means and the third quantity determined by the third detecting means, and determining a fourth quantity indicative of an influence of the first radiation field on biological tissue on the basis of the first quantity determined by the first detecting means and the quantity for adjusting the first quantity. Preferably, the biological tissue is human tissue. Preferably, the quantity for adjusting the first quantity is determined in real time. Preferably, the first detecting means and the second detecting means are located at spatially separated locations.

Preferably, the first quantity is a quantity indicative of an influence of the first radiation field on biological tissue and the third quantity is a quantity indicative of an influence of the second radiation field on biological tissue. Further preferably, the first quantity is a dose equivalent and the third quantity is a dose equivalent.

The method may further comprise determining a position of a first unit having the first detecting means, transmitting the first quantity and the determined position to a second unit having the second and third detecting means, and determining a function indicative of an intensity of the first radiation field in dependence on the position of the first unit, on the basis of the first quantity and the determined position of the first unit.

Preferably, the method further comprises detecting a mechanic shack of the first unit, and correcting the first quantity determined by the first detecting means for an influence of the mechanic shock of the first unit.

Further, the method may comprise receiving the first unit in mounting means of the second unit, charging a battery of the first unit and/or performing read and/or write operations to or from a memory of the first unit.

According to a further preferred embodiment of the present invention, a mobile dosimeter unit suitable for use in a dosimeter system for determining radiation exposure comprises a detecting means having a group of at least three detecting devices with a first detecting device, a second detecting device and a third detecting device, and processing means for processing outputs of the first to third detecting devices, wherein the first detecting device is configured for detecting a first variable related to an ionizing particle incident on the first detecting device, wherein the first detecting device has a first range in which the first variable can be detected, wherein the second detecting device is configured for detecting a second variable related to an ionizing particle incident on the second detecting device, wherein the second detecting device has a second range in which the second variable can be detected, wherein the third detecting device is configured for detecting a third variable related to an ionizing particle incident on the third detecting device, wherein the third detecting device has a third range in which the third variable can be detected, wherein a range obtained by combining the first and second ranges is fully contained in the third range, and wherein the processing means is configured to obtain a quantity indicative of an influence of a radiation field comprising ionizing particles at the location of the mobile dosimeter unit on the basis of outputs of the first, second and third detecting devices. Preferably, the first and second detecting devices are configured so that a range obtained by combining the first and second ranges consists of a first sub-range covered by the first detecting device only, a second sub-range covered by the second detecting device only, and a third sub-range covered by both the first and second detecting devices. Further preferably, the first variable, the second variable and the third variable are a deposited energy or a linear energy transfer.

The group of at least three detecting devices may further comprise a fourth detecting device configured for detecting a time-integrated value of a fourth variable related to an ionizing particle incident on the fourth detecting device. Preferably, the fourth variable is an energy deposited in the fourth detecting device, and the fourth detecting device is configured for detecting a total energy that is deposited in the fourth detecting device by ionizing particles incident on the fourth detecting device over time.

Further, the quantity indicative of the influence of the radiation field comprising ionizing particles may be indicative of at least one of a dose equivalent, an energy deposited by an ionizing particle, a spectrum of energies deposited by ionizing particles, a linear energy transfer by an ionizing particle, and a spectrum of linear energy transfers by ionizing particles.

Preferably, the mobile dosimeter unit further comprises means for determining the position of the mobile dosimeter unit, wherein the mobile dosimeter unit is configured to determine, on the basis of the determined quantity indicative of the influence of the radiation field comprising ionizing particles and the determined position, a function indicative of an intensity of the radiation field comprising ionizing particles in dependence on position.

A particular advantage is achieved if the mobile dosimeter unit further comprises a shock detector configured for detecting a mechanic shock of the mobile dosimeter unit, and means for correcting the output of the detecting devices included by the detecting means for an influence of the mechanic shock of the mobile dosimeter unit detected by the shock detector.

According to a further preferred embodiment of the present invention, a dosimeter system for determining radiation exposure comprises a plurality of first units and a second unit, wherein each of the first units comprises detecting means configured for determining a quantity indicative of an influence of a radiation field present at a position of the respective first unit, means for determining the position of the respective first unit, and transmitting means for transmitting the quantity determined by the detecting means and the determined position of the respective first unit to the second unit, wherein the second unit comprises means for determining a function indicating an intensity of the radiation field in which the plurality of first units are present in dependence on position on the basis of the quantities and positions of the plurality of first units received by the second unit from the plurality of first units. The dosimeter system may comprise a plurality of second units, and the transmitting means of each first unit may be configured for transmitting the quantity determined by the detecting means and the determined position of the respective first unit to more than one of the plurality of second units.

Preferably, the detecting means comprises a first detecting device configured for detecting a first variable related to an ionizing particle incident on the first detecting device, and the first detecting device has a first range in which the first variable can be detected. Further preferably, the detecting means further comprises a second detecting device configured for detecting a second variable related to an ionizing particle incident on the second detecting device, the second detecting device has a second range in which the second variable can be detected, and the detecting means is configured to obtain the first quantity on the basis of an output of the first and second detecting devices. Yet further preferably, the first and second detecting devices are configured so that a range obtained by combining the first and second ranges consists of a first sub-range covered by the first detecting device only, a second sub-range covered by the second detecting device only, and a third sub-range covered by both the first and second detecting devices. Therein, the first variable and the second variable preferably are a deposited energy or a linear energy transfer. Yet further preferably, the detecting means further comprises a third detecting device configured for detecting a third variable related to an ionizing particle incident on the third detecting device, the third detecting device has a third range in which the third variable can be detected, a range obtained by combining the first and second ranges is fully contained in the third range, and the detecting means is configured to obtain the first quantity on the basis of an output of the first, second and third detecting devices. Therein, the third variable preferably is a deposited energy or linear energy transfer.

The detecting means may further comprise a fourth detecting device configured for detecting a time-integrated value of a fourth variable related to an ionizing particle incident on the fourth detecting device. Preferably, the fourth variable is an energy deposited in the fourth detecting device, and the fourth detecting device is configured for detecting a total energy that is deposited in the fourth detecting device by ionizing particles incident on the fourth detecting device over time.

Further, each of the first units may comprise a shock detector configured for detecting a mechanic shock of the respective first unit, and means for correcting the quantity determined by the respective detecting means for an influence of the mechanic shock of the respective first unit detected by the respective shock detector.

It is preferred that the second unit comprises mounting means configured for receiving a first unit of the plurality of first units in the mounting means, for charging a battery of the first unit and/or for read or write operations to or from a memory of the first unit.

DETAILED DESCRIPTION OF THE INVENTION

Preferred embodiments of the present invention will be described in the following with reference to the accompanying figures, wherein identical objects in the figures are indicated by identical reference numbers. It is understood that the present invention shall not be limited to the described embodiments, and that the described features and aspects of the embodiments may be modified or combined to form further embodiments of the present invention.

Figure 1:
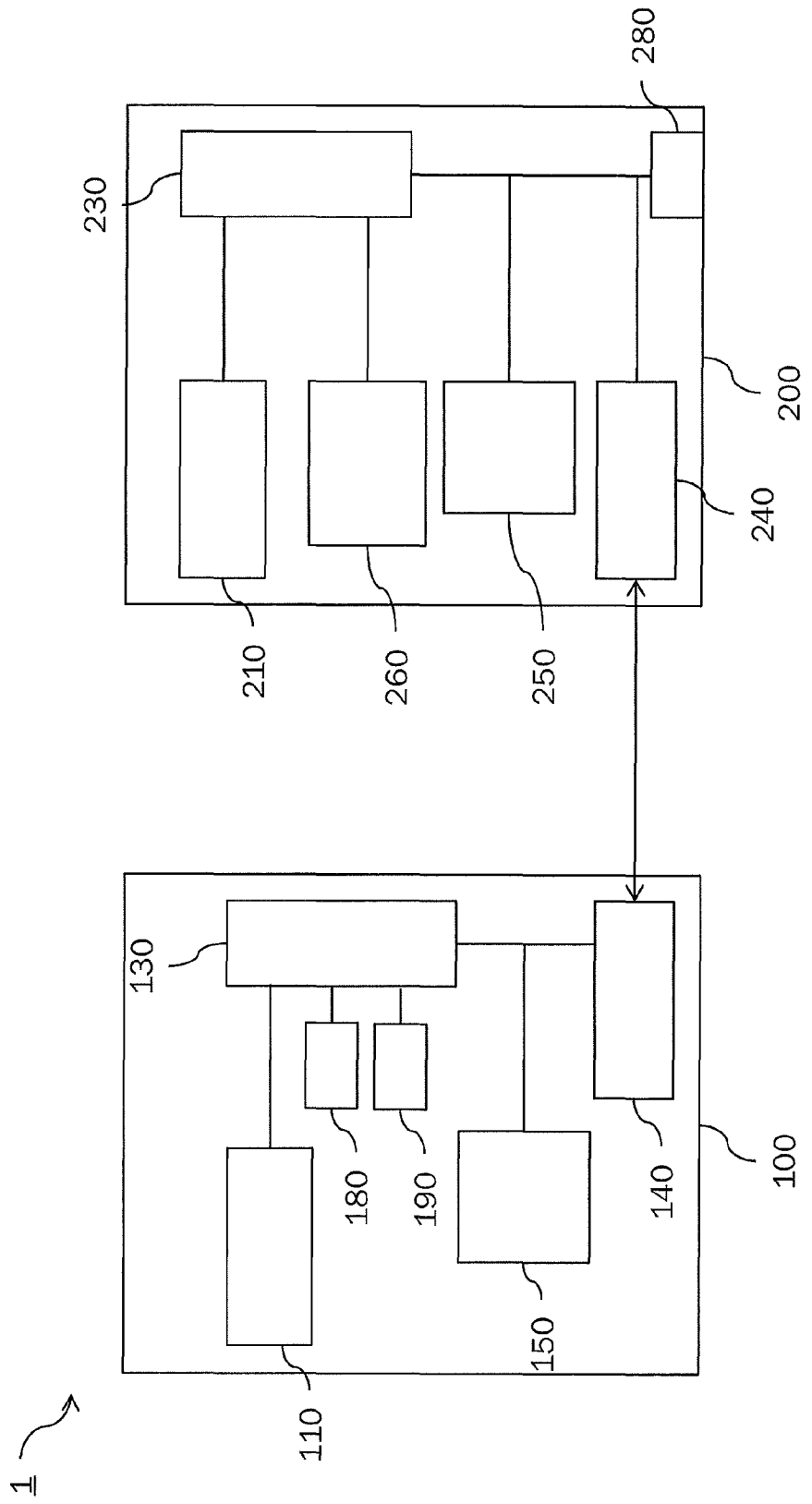
FIG. 1 is a schematic view of an embodiment of the inventive dosimeter system comprising a mobile unit and a main unit.

FIG. 1 gives a schematic view of an embodiment of the inventive dosimeter system 1 comprising a mobile unit 100 (mobile dosimeter unit or first unit) for personal dosimetry in the framework of health monitoring and radiation protection, and a main unit 200 (second unit) for environmental monitoring, cross referencing, data storage and processing.

Figure 8A:
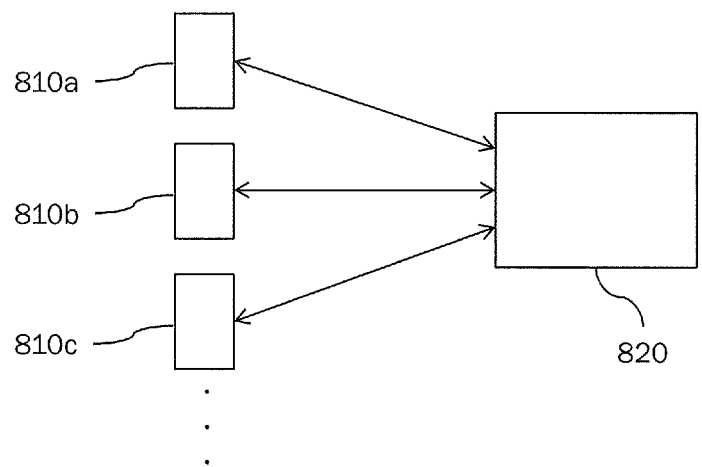
FIGS. 8A and 8B are schematic views of a dosimeter system according to embodiments of the present invention.
Figure 8B:
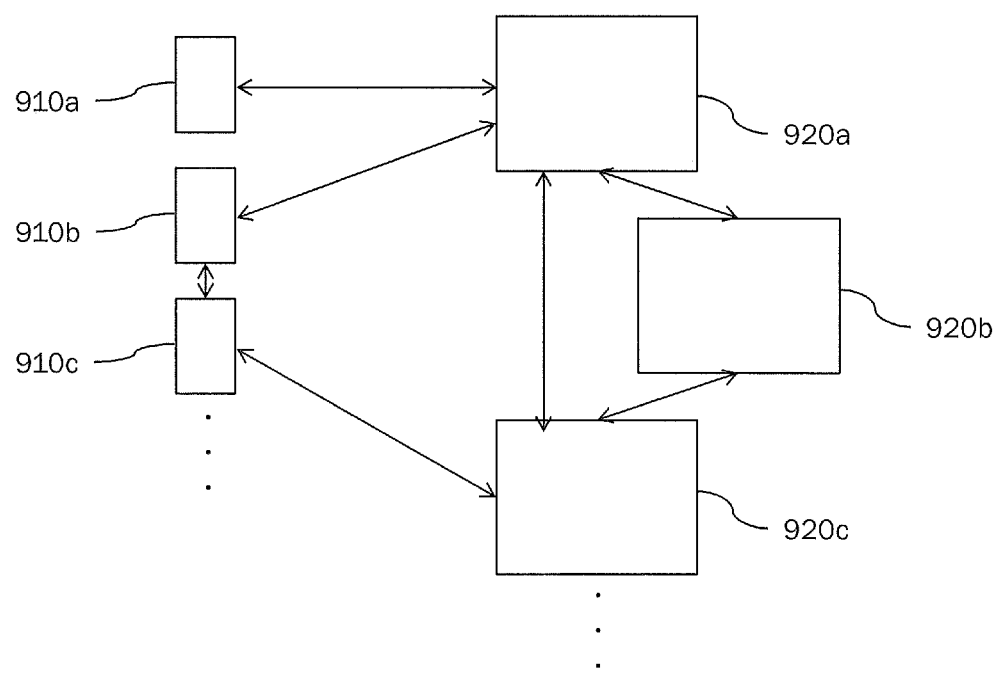

Although FIG. 1 shows a single mobile unit 100 and a single main unit 200, the dosimeter system may comprise a plurality of N mobile units 810a, 810b, 810c; 910a, 910b, 910c and a plurality of M main units 920a, 920b, 920c as illustrated in FIG. 8A and FIG. 8B. In such a system, it is understood that each of the N mobile units 810a, 810b, 810c; 910a, 910b, 910c may exchange information with each other of the N mobile units 810a, 810b, 810c; 910a, 910b, 910c as well as with each of the M main units 920a, 920b, 920c. Likewise, each of the M main units 920a, 920b, 920c may exchange information with each other of the M main units 920a, 920b, 920c as well as with each of the N mobile units 810a, 810b, 810c; 910a, 910b, 910c.

The mobile unit 100 is an active dosimeter and is to be worn or carried by a person the radiation exposure of whom is to be monitored (relevant person under surveillance). The mobile unit 100 and the main unit 200 are preferably (but not necessarily) used in relative proximity to each other, e.g. within a range of wireless transmission, so that a first radiation field and a second radiation field in which the mobile unit 100 and the main unit 200, respectively, are present, substantially have the same nature. That is, the first radiation field and the second radiation field have substantially the same particle composition, and substantially the same spectrum of particle energies. Intensities of the first and second radiation fields (i.e. particle fluxes) however can be different from each other without affecting operation of the inventive dosimeter system.

The mobile unit 100 comprises first detecting means 110 having first measuring circuitry 120 (not shown in FIG. 1, cf. FIG. 3), a processing unit 130 (processing means), transmitting means 140, a shock detector 180, a position sensor 190 (means for determining a position of the mobile unit), and an output device 150. Further, the mobile unit 100 comprises a battery (not shown) for sustaining operation of the mobile unit 100, a non-volatile memory (not shown) for storing data collected by the mobile unit 100 and a hardware interface (not shown) for connecting the mobile unit 100 to the main unit 200.

The first detecting means 110 is sensitive to radiation and outputs a first quantity indicative of an influence of a first radiation field, wherein the first radiation field is a radiation field in which the mobile unit 100 is present. To this end, the first detecting means 110 includes detecting devices each comprising a material that is reactive to radiation, such as silicon, doped silicon, or any other semiconductor material. Further, the material may be a gas, such as nitrogen, inside a gas-filled chamber of the first detecting means 110.

Depending on the concrete implementation of the first detecting means 110, which will be described in more detail below, the first quantity relates to at least one of an energy deposited in the first detecting means by an ionizing particle (in units of Gray, 1 Gy=1 J/kg), a linear energy transfer to the first detecting means 110 by an ionizing particle (in units of keV/μm), a spectrum of energies deposited in the first detecting means 110 by a plurality of ionizing particles, a spectrum of linear energy transfers to the first detecting means 110, and a dose equivalent (in units of Sievert, 1 Sv=1 J/kg). Preferably, the spectrum of energies deposited in the first detecting means 110 relates to a predetermined period of time. In a preferred embodiment, the first quantity relates to a dose equivalent, and in particular to a dose equivalent received during the predetermined period of time.

In the context of this description, the term "ionizing particles" refers to particles such as protons, helium ions, electrons, heavy ions, photons (gamma radiation) or neutrons. The term "spectrum of energies" refers to a number of events for each of a plurality of bins relating to a given amount of energy deposited in the first detecting means 110, and the term "spectrum of linear energy transfers" refers to a number of events for each of a plurality of bins relating to a given amount of linear energy transfer to the first detecting means 110. Further, the terms "ionizing particles" and "ionizing radiation" may be used interchangeably.

The first measuring circuitry 120 of the first detecting means 110 controls measurement performed by the first detecting means 110 by controlling the operation parameters of the first detection means 110 on the basis of commands issued by the processing unit 130 which is connected to the first detecting means 110. The processing unit 130 may be a microcontroller. Further, the first measuring circuitry 120 receives an output of individual so detecting devices (not shown) of the first detecting means 110, performs processing of the outputs and provides the first quantity as an output of the first detecting means 110 on the basis of the processing of the outputs of the detecting devices. The first quantity is provided to the processing unit 130 in a suitable data format. Although indicated as comprised by the first detecting means 110, the first measuring circuitry 120 may also be an entity distinct from the first detecting means 110. Further details relating to the individual detecting devices will be provided below in connection with FIG. 3.

For reasons of energy conservation (battery conservation), the digital electronics of the mobile unit 100 is normally in a sleep mode and is woken up with a short response time upon particle detection in the first detecting means 110 so that no particle is lost, i.e. no information about the radiation field is lost. Further details relating to this issue will be provided below in connection with FIG. 3.

The processing unit 130 is configured to issue commands to the first measuring circuitry 120 of the first detecting means 110 for controlling the operation parameters of the first detection means 110. These operation parameters relate to operation parameters of the individual detecting devices of the first detecting means 110. Further, the processing unit 130 is configured to monitor a battery status of the battery of the mobile unit 100, control communication with the main unit 200 via transmitting means 140, store the first quantity to the memory of the mobile unit 100, control the output device 150 of the mobile unit 100, and correct the output of the detecting devices of the first detecting means 110 for effects that are due to mechanic shock detected by the shock detector 180.

Correction of the output of the detecting devices of the first detecting means 110 for effects that are due to mechanic shock will now be described in detail.

Typical detecting devices such as silicon diodes are known to produce spurious outputs when subjected to mechanic shock. In order to correct for these spurious outputs, a piezoelectric element is attached to a housing of the mobile unit 100 as the shock detector 180. This shock detector 180 can detect mechanic shock to which the mobile unit 100 is subjected and can thus be used to discriminate outputs resulting from radiation against outputs of the first detecting means 110 that occur simultaneously with the detected mechanical shock. The sensitivity of the shock detector 180 is set to a level so that the mechanic shock is detected slightly before it causes a spurious output of the first detecting means 110. Once the mechanic shock has been detected, the shock detector 180 outputs a respective signal to the processing unit 130 indicating that the mechanic shock has occurred. The first detecting means 110 is instructed by the processing unit 130 to ignore events detected by any of the detecting devices of the first detecting means 110 immediately after reception of this signal. Alternatively, removal of events detected by any of the detecting devices of the first detecting means 110 immediately after reception of this signal is performed in the processing unit 130. Accordingly, an output of the first detecting means 110 can be corrected for spurious elements. In this sense, the processing unit 130 acts as means for correcting the first quantity determined by the first detecting means 110 for an influence of the mechanic shock of the mobile unit 100 detected by the shock detector 180.

The processing unit 130 provides the first quantity to the transmitting means 140. In reaction thereto, the transmitting means 140 transmits the first quantity to the main unit 200, e.g. via wireless connection or via any other communication means suitable for the purpose. According to the invention, transmission may take place periodically, preferably once for each predetermined period of time. As indicated above, the first quantity transmitted by the transmitting means 140 corresponds to the predetermined period of time, wherein the predetermined period of time preferably corresponds to a predetermined period between consecutive transmissions. In other words, if the first quantity is indicative of a dose equivalent, it corresponds to a dose equivalent that has been received during the predetermined period of time. Preferably, the predetermined period of time and the predetermined period between consecutive transmissions are chosen to be in a range from seconds to minutes (e.g. one second to one minute), so that respective values of the first quantity can be said to be transmitted to the main unit 200 in real time. In the event of high or low count rates (event rates), the predetermined period of time (i.e. an integration time) and the predetermined period between consecutive transmissions can be adjusted by the processing unit 130 in accordance with an event rate in order to allow for obtaining reasonable statistics. For instance, if the event rate is found to be low, the period of time and the period between consecutive transmissions can be increased, and for a high event rate the period of time and the period between consecutive transmissions can be reduced.

After transmission of the first quantity, the first quantity in the mobile unit 100 is reset. In addition, an integrated value of the first quantity (e.g. an integrated dose equivalent) may be maintained in the memory of the mobile unit 100. Further, each value of the first quantity transmitted by the transmitting means 140 may be stored in the memory of the mobile unit 100 for later readout. Alternatively, it is also possible to transmit the integrated value of the first quantity to the main unit 200. In this case, the first quantity corresponding to a respective predetermined period of time needs to be determined in the main unit 200 by taking a difference between subsequently received integrated values of the first quantity.

The first quantity transmitted by the transmitting means 140 is received by receiving means 240 of the main unit 200. It is understood that the transmitting means 140 of the mobile unit 100 can also function as a receiving means, and that the receiving means 240 of the main unit 200 can also function as a transmitting means.

The mobile unit 100 further comprises the position sensor 190, which can be a GNSS receiver, e.g. a GPS receiver or a Galileo receiver, or any other means capable of determining the global position of the mobile unit 100. The position determined by the position sensor 190 is transmitted to the main unit 200 via the transmitting means 140 together with the first quantity determined by the first detecting means 110. Accordingly, the main unit 200 receives pairs of values that are of type (first quantity, corresponding position) for each predetermined period of time.

The mobile unit 100 further comprises the output device 150 which can be a display used to display any or all of the first quantity, a warning message indicating critical levels of received dose equivalent, a message or quantity received from the main unit 200, or the position of the mobile unit 100 determined by the position sensor 190. Of course, also display of further information relating to a status of the mobile unit 100 by the output device 150 is possible.

In addition, the mobile unit 100 may comprise a connection interface that allows connection of external hardware, such as additional detecting means in order to enhance the detection capabilities of the mobile unit 100. For instance, also a further mobile unit 100 may be connected to the connection interface. The connection interface may be a wireless interface. Provision of the connection interface also allows integration of plural mobile units 100 into a compound mobile unit, in order to obtain a higher performance.

In the above description of the mobile unit 100, the mobile unit 100 comprises a single first detecting means 110, details of which are described below in connection with FIG. 3. However, applying higher integration techniques, the mobile unit 100 may comprise a plurality of first detecting means 110 (or a plurality of detecting devices) in order to allow for redundancy in the mobile unit 100 or for a higher performance of the mobile unit 100.

The main unit 200 (second unit) comprises second detecting means 210 having second measuring circuitry 220 (not shown in FIG. 1, cf. FIG. 7), a processing unit 230 (processing means), third detecting means 260 having third measuring circuitry (not shown), the receiving means 240, an output device 250, mounting means 280, and a non-volatile memory (not shown) for storing data collected by the main unit 200 or received from the mobile unit 100.

The second detecting means 210 is sensitive to radiation and is particularly configured to simulate biological tissue, preferably human tissue (i.e. the physiological impact of radiation on biological tissue, preferably human tissue). The second detecting means 210 thus outputs a dose equivalent resulting from exposure to a second radiation field (i.e. a second quantity indicative of an influence of a second radiation field on biological tissue, preferably human tissue), wherein the second radiation field is a radiation field in which the main unit 200 is present. In more detail, the second detecting means 210 according to this embodiment is a tissue equivalent proportional counter (TEPC).

The TEPC provides a reference measurement of the second radiation field in that it is capable of measuring a dose equivalent, a lineal energy deposition spectrum (spectrum of linear energy transfers) and a mean Q factor of a radiation field. It consists of a TEPC head and readout electronics (second measuring circuitry 220). The TEPC head consists of a spherical sealed ionization chamber filled with a gas at low pressure and a front-end amplifier. Due to the low pressure of the gas, the ionizing chamber simulates a given volume of human tissue, e.g. a sphere of human tissue having a diameter of 1 μm.

The TEPC is capable of detecting both charged and neutral particles. As charged particles interact with a wall material of the ionization chamber, ionization occurs within a detection volume enclosed by the ionization chamber and free electrons drift to a positively biased anode wire inside the ionization chamber. Collisions of the electrons with other gas molecules inside the ionization chamber generate additional ion pairs. The charge detected at the anode wire is then proportional to the energy deposition of the measured radiation, wherein the energy deposition is determined by pulse height analysis of the detected signal. Lineal energy is determined by dividing the energy deposition by the mean path length, which is determined by the dimension of the ionizing chamber. For a spherical ionization chamber the mean path length is ⅔ of the diameter of the ionization chamber.

The front end amplifier is placed adjacent to the ionization chamber, as close to the ionization chamber as possible, in order to avoid possible noise pickup on a signal path between the ionization chamber and the front end amplifier. It is formed of a charge sensitive amplifier and is followed by a shaping amplifier. The charge sensitive amplifier integrates the signal detected by the ionizing chamber, thus converting the charge detected at the anode wire into a voltage amplitude. The deposited energy is represented by the pulse height of the voltage amplitude. The shaping amplifier is formed by a second-order band-pass filter and is sensitive to sharp voltage steps and suppresses noise. The output of the shaping amplifier represents the energy deposited by the respective particle in the ionizing chamber. As the ionizing chamber simulates a given volume of human tissue, the deposited energy weighted with a lineal energy spectrum corresponds to a dose equivalent.

Each lineal energy corresponds to a known (and pre-stored, e.g. in a table) Q factor, so that by taking spectra of lineal energies, a mean Q factor of the radiation field can be determined. The mean Q factor determined by the TEPC can then be used to obtain an estimation of a dose equivalent from an absorbed dose determined in the mobile unit 100. Therein, it is however to be noted that in general also the mobile unit 100 is capable of determining a mean Q factor.

The third detecting means 260 is of the same type as the first detecting means 110 of the mobile unit 100. The third detecting means 260 outputs a third quantity indicative of an influence of the second radiation field. For further details on the third detecting means 260 it is referred to the above description of the first detecting means 110.

Depending on the concrete implementation of the third detecting means 260 (which is identical to the concrete implementation of the first detecting means 110), the third quantity relates to at least one of an energy deposited in the third detecting means by an ionizing particle (in units of Gray), a linear energy transfer to the third detecting means by an ionizing particle (in units of keV/μm), a spectrum of energies deposited in the third detecting means by a plurality of ionizing particles, a spectrum of linear energy transfers to the third detecting means, and a dose equivalent (in units of Sievert). Preferably, but not necessarily, the type of the third quantity is identical to the type of the first quantity, e.g. if the first quantity is a dose equivalent, also the third quantity is a dose equivalent. Preferably, the spectrum of energies deposited in the first detecting means 110 relates to a predetermined period of time. Preferably, the third quantity relates to a dose equivalent, and in particular to a dose equivalent received during the predetermined period of time.

The third measuring circuitry of the third detecting means 260 controls measurement performed by the third detecting means 260 by controlling the operation parameters of the third detection means 260 on the basis of commands issued by the processing unit 230, such as a microcontroller, which is connected to the third detecting means 260. Further, the third measuring circuitry receives an output of individual detecting devices (not shown) of the third detecting means 260, performs processing of the outputs and provides the third quantity as an output of the third detecting means 260 on the basis of the processing of the outputs of the detecting devices. The third quantity is provided to the processing unit 230 in a suitable data format. Although indicated as comprised by the third detecting means 260, the third measuring circuitry may also be an entity distinct from the third detecting means 260.

The processing unit 230 is configured to issue commands to the third measuring circuitry of the third detecting means 260 for controlling the operation parameters of the third detection means 260. These operation parameters relate to operation parameters of the individual detecting devices of the third detecting means 260. Further, the processing unit 230 is configured to control communication with the mobile unit 100 via receiving means 240, and control the output device 250 of the main unit 200. If mechanic shock of the main unit 200 is to be expected, the processing unit 230 may be further configured to correct the output of the detecting devices of the third detecting means 260 for effects that are due to mechanic shock detected by a shock detector of the main unit 200 (not shown). For the function of the shock detector of the main unit 200 it is referred to the discussion of the shock detector 180 of the mobile unit 100.

In the following, an operation of the processing unit 230 as means for determining a quantity for adjusting the first quantity on the basis of the second quantity determined by the second detecting means 210 and the third quantity determined by the third detecting means 260 will be described. Alternatively, separate means for determining the quantity for adjusting the first quantity on the basis of the second quantity determined by the second detecting means 210 and the third quantity determined by the third detecting means 260 may be provided in the main unit 200.

Said operation of the processing unit 230 is performed whenever a first quantity is received from the mobile unit 100. In other words, if the mobile unit 100 transmits the first quantity with a given periodicity of transmission (corresponding to a given rate of transmission), said operation of the processing unit 230 is executed with the same periodicity (rate). Thus, since transmission of the first quantity to the main unit 200 occurs in real time, also the below determination of a quantity for adjusting the first quantity can be said to occur in real time.

The processing unit 230 receives the first quantity from the receiving means 240. If the first quantity is not a dose equivalent (per predetermined period of time) the first quantity is translated into a dose equivalent (per predetermined period of time). This is achieved by referring to pre-calculated or pre-stored Q factors corresponding to respective linear energy transfers, and, if necessary, to a known mean path length of the respective detecting devices of the first detecting means 110. If necessary, also the third quantity is translated into a dose equivalent (per predetermined period of time). According to the preferred embodiment of the invention however, the first quantity as well as the third quantity are indicative of a dose equivalent per the predetermined period of time.

The processing unit 230 then compares the dose equivalent indicated by the third quantity to the dose equivalent indicated by the second quantity. If the calibration of the third detecting means 260 (which is identical to the calibration of the first detecting means 110) is suitable for the second radiation field, the dose equivalent indicated by the third quantity and the dose equivalent indicated by the second quantity are expected to coincide within a given margin. If however the actual nature of the second radiation field turns out to be different from its expected nature, so that the calibration of the third detecting means 260 is not suited for the second radiation field, the respective dose equivalents are expected to deviate from each other. Typically, in such cases the dose equivalent detected by the second detecting means 210 is larger than the dose equivalent indicated by the third quantity determined by the third detecting means 260.

Since the first and second radiation fields are similar as regards their nature, there is a risk that the dose equivalent (or more generally, the first quantity) determined by the first detecting means 110 is also too low. Thus, in case of a deviation of the dose equivalent indicated by the third quantity from the dose equivalent indicated by the second quantity, a quantity for adjusting the first quantity is determined on the basis of the third quantity and the second quantity. More precisely, the quantity for adjusting the first quantity is determined on the basis of the dose equivalent indicated by the third quantity and the dose equivalent indicated by the second quantity. Therein, the quantity for adjusting the first quantity may be a dose equivalent that can be added to the dose equivalent indicated by the first quantity and that is determined by taking a difference between the dose equivalent indicated by the second quantity and the dose equivalent indicated by the third quantity.

If the dose equivalent indicated by the first quantity and the dose equivalent indicated by the third quantity are found to be different beyond a predetermined threshold, it is concluded that the intensity of the first radiation field (corresponding e.g. to an overall particle flux) is different from the intensity of the second radiation field. In this case it may not be appropriate to simply add a dose equivalent to the dose equivalent indicated by the first quantity as described above. Therefore, if the dose equivalent indicated by the first quantity and the dose equivalent indicated by the third quantity are found to be different beyond the predetermined threshold, it is proceeded as follows. First, the difference between the dose equivalent indicated by the second quantity and the dose equivalent indicated by the third quantity is taken. Second, a ratio between the dose equivalent indicated by the first quantity and the dose equivalent indicated by the third quantity is taken. Third, the dose equivalent to be added to the dose equivalent indicated by the first quantity is determined by multiplying the obtained ratio with the obtained difference.

Alternatively, the quantity for adjusting the first quantity may also be a factor by which the dose equivalent indicated by the first quantity is to be multiplied. The present invention shall not be considered as limited to the above implementations of the quantity for adjusting the first quantity.

By determining the quantity for adjusting the first quantity, it is ensured that the dose equivalent received by a person under surveillance (a carrier of the mobile unit 100) can be determined correctly and accurately, regardless of a particular (potentially unexpected) nature of the radiation field in which the person under surveillance is present. Advantageously, the correct and accurate dose equivalent received by the person under surveillance can be obtained in real time.

Since the first and third detecting means 110, 260 are of the same type, the testing of the calibration of the first detecting means 110, i.e. the determination of the quantity for adjusting the first quantity, is not affected by systematic errors. Any systematic mismatch between the actual dose equivalent and the dose equivalent indicated by the first quantity is taken into account by the quantity for adjusting the first quantity if it is determined as outlined above. Further, also aging and deterioration effects of the first detecting means 110 (including the first measuring circuitry 120) are automatically taken into account. For instance, a discrepancy between the actual dose equivalent and the dose equivalent indicated by the first quantity that grows with time due to a deterioration of the first detecting means 110 is also present in the third detecting means 260 and therefore automatically taken into account. This advantage is achieved to its fullest extent if the first detecting means 110 and the third detecting means 260 are replaced simultaneously.

After obtaining the quantity for adjusting the first quantity, the processing unit 230 may continue to determine a fourth quantity indicative of an influence of the first radiation field on biological tissue, e.g. human tissue on the basis of the first quantity determined by the first detecting means 110 and the quantity for adjusting the first quantity. In the cases described above, this is achieved by adding the dose equivalent indicated by the quantity for adjusting the first quantity to the dose equivalent indicated by the first quantity or by multiplying the dose equivalent indicated by the first quantity with the quantity for adjusting the first quantity. Alternatively, also separate means for performing this task may be provided in the main unit 200.

Instead of determining the fourth quantity in the main unit 200, the quantity for adjusting the first quantity may also be transmitted to the mobile unit 100, and the fourth quantity may then be determined by respective means, such as the processing unit 130 in the mobile unit 100. Of course, it is also possible to determine the fourth quantity in the mobile unit 100 and in the main unit 200 simultaneously. If the fourth quantity is only determined in the main unit 200, an alert message and/or an alarm may be issued to the mobile unit 100 if the determined fourth quantity exceeds a predetermined threshold for a received dose equivalent per the predetermined period of time.

If the first through third quantities correspond to the predetermined period of time, the main unit 200 stores an integrated value of the fourth quantity in its memory, i.e. a value that corresponds to the sum of all previously obtained fourth quantities. Preferably, also the mobile unit 100 stores an integrated value of the fourth quantity in its memory.

As described above, the mobile unit 100 comprises the position sensor 190 capable of determining the global position of the mobile unit 100. The determined position is transmitted to the main unit 200 together with the first quantity, so that the main unit 200 receives pairs of values of type (first quantity, corresponding position). These pairs of values are provided to the processing unit 230 of the main unit 200. Thus, by collecting consecutive pairs of values received from the mobile unit 100, the processing unit 230 can record a trajectory of the mobile unit 100 in space, and values of the first quantity along the trajectory. Preferably, the predetermined period of time and correspondingly the periodicity of transmission are chosen so that a resolution of the recorded trajectory is in the sub-meter range.

Since the mobile unit 100 is typically carried at the front of the body of the relevant person under surveillance, e.g. attached to a belt, the problem arises that depending on a direction from which the radiation is incident on the person under surveillance, a shielding of radiation by the body of the person under surveillance may occur. That is, if the person under surveillance is facing towards a source of radiation, the first quantity output by the first detecting means 110 is larger than when the person under surveillance is facing away from the source of radiation, since in the latter case shielding of the radiation from the mobile unit 100 by the body of the person under surveillance occurs. Analyzing the received pairs of values of type (first quantity, corresponding position), an orientation of the person under surveillance (i.e. a facing direction) may be inferred. On the basis of the facing direction, a direction of incidence of the radiation on the person under surveillance may be inferred, and a correction for the shielding of the mobile unit 100 from the radiation by the body of the person under surveillance may be performed. Accordingly, an accurate dose equivalent actually received by the person under surveillance may be determined.

The trajectory together with values of the first quantity along the trajectory represents a (discrete) function mapping coordinates in 3D space to values of the first quantity, or correspondingly, values indicative of an intensity of the first radiation field. By interpolating between pairs of values, a continuous function can be obtained. As time passes, the recorded trajectory covers more and more of the space in which the relevant person under surveillance is operating, and a more complete picture of a spatial dependence of the intensity of the first radiation field is obtained. In particular, by interpolation, a function can be obtained that maps any 3D-coordinate within the space in which the person under surveillance is operating to a value of the first quantity, or correspondingly, to an intensity of the first radiation field. In this sense, the processing unit 230 of the main unit 200 functions as means for determining a function indicative of an intensity of the first radiation field in dependence on the position of the mobile unit 100.

In one embodiment, as shown in FIG. 8A, the dosimeter system 1 comprises a main unit 820 and a plurality of mobile units 810a, 810b, 810c, wherein each of the mobile units 810a, 810b, 810c is of a configuration as described above, and each of the mobile units 810a, 810b, 810c periodically transmits a first quantity and a determined position to the main unit 820. In this case, a trajectory as described above can be recorded for each of the plurality of mobile units 810a, 810b, 810c and the recorded trajectories can be combined by the processing unit 230 of the main unit 820 in order to obtain the function mapping 3D-coordinates to values of the first quantity and correspondingly to an intensity of the first radiation field more accurately and more quickly.

The main unit 200 may store any or all of the first quantity received from the mobile unit 100, the second quantity, the third quantity, the fourth quantity, and integrated values of any of the aforementioned quantities in the memory of the main unit 200. Therein, it is to be noted that in the presence of plural mobile units, a distinct data record comprising any or all of the above data items is kept for each mobile unit in the memory of the main unit 200. Also, if it is known that mobile units are to be handed over from a first relevant person under surveillance (user) to a second relevant person under surveillance (user), distinct data records are kept for each user in the memory of the main unit 200.

The main unit 200 further comprises the display device 250 which can be used to display any or all of the first quantity received from the mobile unit 100, the second quantity, the third quantity, the fourth quantity, integrated values of any of the aforementioned quantities, and the alert message. Further, by the display device 250, the data record of any mobile unit or any user may be displayed. Accordingly, each user may e.g. view the history of his personal accumulated dose in graphical form, check the measured history of the spectrum of the energy, or change a configuration of his respective mobile unit 100 to fit the current purpose in the most optimal way.

Of course, also display of further information relating to a status of the main unit 200, the mobile unit 100 or the plurality of mobile units by the output device 250 is possible.

By the receiving means 240, the main unit 200 can also transmit any or all of the above data items and data records to an external computing device (third unit) for post-operation analysis of the respective data, and/or for backup of the respective data. Further, by the receiving means 240, the main unit 200 can update the firmware and software of the mobile unit 100, and perform online calibration of the mobile unit 100, Further, through the receiving means 240, remote maintenance, remote control, software and firmware update, as well as re-booting of the main unit 200 may be performed.

The mounting means 280 of the main unit 200 includes a slot for physically receiving at least a portion of the mobile unit 100, and a hardware interface (a communication link) for connecting to the hardware interface of the mobile unit 100. The combination of the slot and the hardware interface of the main unit 200 is referred to as a mobile unit reader head.

The mobile unit reader head provides a communication link between the mobile unit 100 and the main unit 200 (more specifically, between the mobile unit 100 and the processing unit 230 of the main unit 200), a power link for charging the battery of the mobile unit 100, and moreover serves as a storage for the mobile unit 100 if it is currently not used.

The mobile unit reader head is a passive electromechanical construction that allows for the connection of the mobile unit to the processing unit 230 of the main unit 200 through a RS-232 HUB device. The communication between the mobile unit 100 and the main unit 200 is based on a proprietary communication protocol with message encapsulation, CRC checksum and packet acknowledgement messages. The mobile unit reader head is connected to a power source of the main unit 200 for providing the charging current to the internal battery of the mobile unit 100 and to the processing unit 230 of the main unit 200.

In a case in which the dosimeter system 1 comprises a plurality of mobile units, the main unit 200 may be provided with more than one mounting means 280. Preferably, the number of mounting means 280 corresponds to the number of mobile units.

In a case in which the dosimeter system 1 comprises a plurality of main units 920a, 920b, 920c, as shown in FIG. 8B, the main units 920a, 920b, 920c may exchange information relating to the second and third quantities between them, or more generally speaking information relating to measurements performed by the respective detecting means of the main units 920a, 920b, 920c. Also, a mobile unit 910a, 910b, 910c currently communicating with a given main unit 920a, 920b, 920c may be handed over to another main unit 920a, 920b, 920c.

Figure 2:
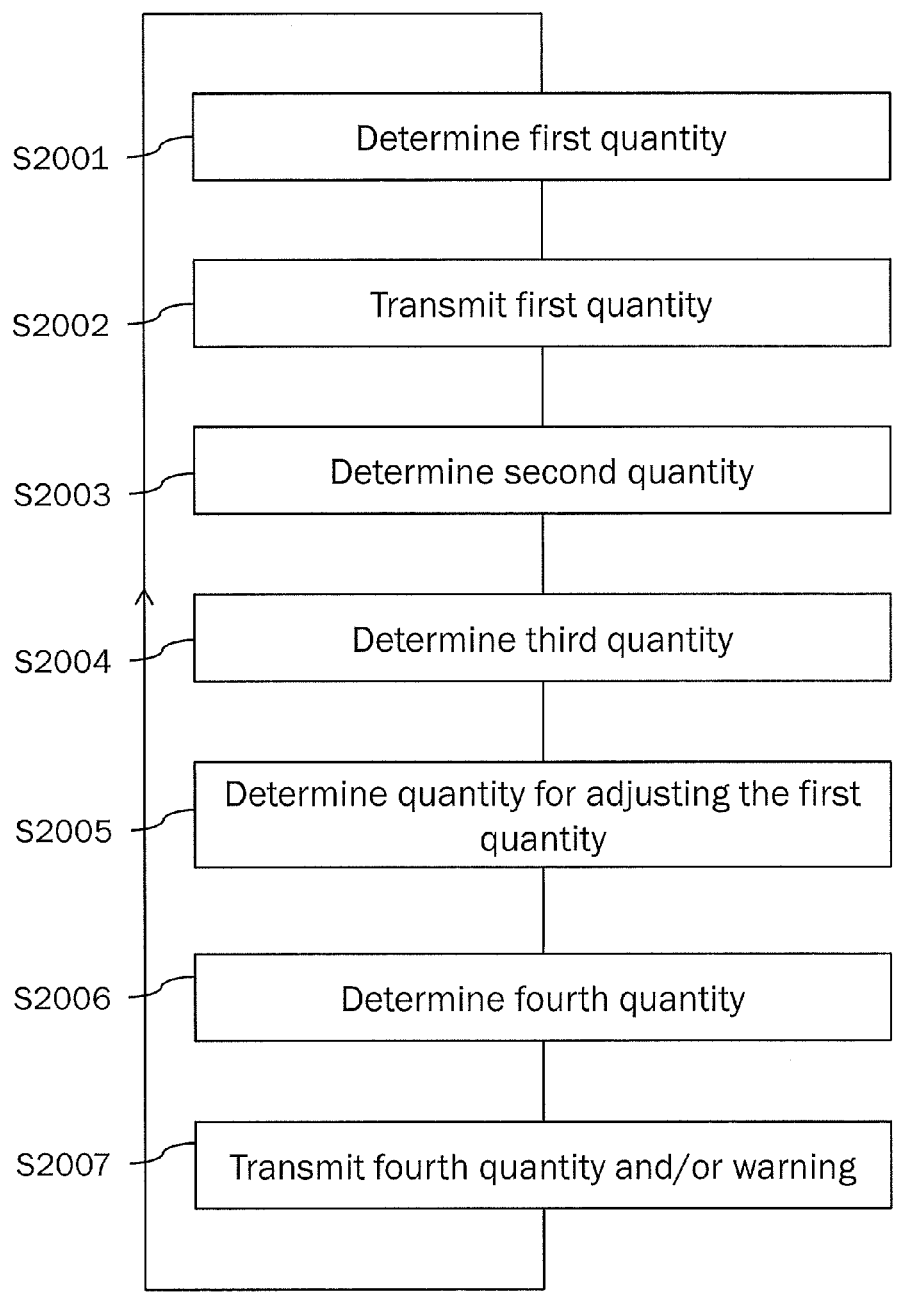
FIG. 2 is a flow chart illustrating operation of the inventive dosimeter system.

Next, with reference to FIG. 2 a method for determining radiation exposure will be described, wherein the method can be understood to correspond to an operation of the inventive dosimeter system 1. It is understood that the below method is performed repeatedly during operation of the dosimeter system 1.

At step S2001, the first quantity indicative of an influence of the first radiation field is determined by the first detecting means 110 of the mobile unit 100. At step S2002, the obtained first quantity is transmitted to the main unit 200. As described above, the transmission can be performed by the transmitting means 140. At step S2003, the second quantity indicative of an influence of the second radiation field on biological tissue, e.g. human tissue is determined by the second detecting means 210 of the main unit 200. At step S2004, the third quantity indicative of an influence of the second radiation field is determined by the third detecting means 260 of the main unit 200. For details on the determination of the first through third quantities it is referred to the below discussion of FIG. 3 and FIG. 4.

In the following discussion, it will be assumed that the first through third quantities (henceforth referred to as Q1, Q2, Q3, respectively) relate to dose equivalents corresponding to equal periods of time, and in particular to the predetermined period of time. For cases in which either of these quantities does not relate to a dose equivalent, the respective quantity can be translated into a dose equivalent by commonly known procedures as discussed above, so that the below discussion is also applicable to these cases.

At step S2005, the quantity A for adjusting the first quantity is determined on the basis of the second quantity and the third quantity. To this end, the second quantity is compared to the third quantity and a difference D23 between these quantities is obtained, D23=Q2−Q3. In an alternative embodiment, a ratio R23 between the second quantity Q2 and the third quantity Q3 is obtained, R23=Q2/Q3. The quantity A for adjusting the first quantity corresponds to the difference D23, or in the alternative embodiment, to the ratio R23.

Next, at step S2006, the fourth quantity Q4 indicative of an influence of the first radiation field on human tissue is obtained on the basis of the first quantity Q1 and the quantity A for adjusting the first quantity. In more detail, the fourth quantity Q4 is obtained by adding the quantity A for adjusting the first quantity to the first quantity Q1, Q4=Q1+A=Q1+(Q2−Q3). In the alternative embodiment, the fourth quantity Q4 is obtained by multiplying the first quantity Q1 by the quantity A for adjusting the first quantity Q1, Q4=Q1·A=Q1·Q2/Q3.

However, as mentioned above, adjustment of the first quantity Q1 is only then performed if there is a deviation between the second quantity Q2 and the third quantity Q3. Thus, if the difference D23 is found to be within a predetermined margin for the difference, or in the alternative embodiment if the ratio R23 is found to be within a predetermined margin for the ratio, the further process according to steps S2005 and S2006 can be omitted. Alternatively, the quantity A for adjusting the first quantity Q1 could be set to 0, or in the alternative embodiment to 1.

In a further alternative embodiment, also the quantity Q1 is taken into account when determining the quantity A for adjusting the first quantity Q1 at step S2005. Accordingly, the quantity A for adjusting the first quantity Q1 is determined on the basis of the first through third quantities Q1, Q2, Q3. In this case, first the second quantity is compared to the third quantity and the difference D23 between these quantities is obtained, D23=Q2−Q3. Second, a ratio R13 between the first and third quantities is obtained, R13=Q1/Q3. Third, the quantity A for adjusting the first quantity is obtained by normalizing the difference D23 to the overall scale of the first quantity, A=D23·R13. The fourth quantity Q4 is then obtained at step S2006 by adding the quantity A for adjusting the first quantity to the first quantity Q1, so that Q4=Q1+A=Q1+Q1/Q3·(Q2−Q3). Thereby, it is ensured that potentially different levels of intensity of the first and second radiation fields are taken into account.

At step S2007, the fourth quantity Q4 and/or a warning message is transmitted to the mobile unit 100.

As an alternative to steps S2006 and S2007, the quantity A for adjusting the first quantity is transmitted to the mobile unit 100 at a step S2006'. In this case, the fourth quantity Q4 is determined in the mobile unit 100 at a step S2007'.

In the above, it is understood that the order of steps is only fixed with regard to steps that are dependent on a result of a previous step. Apart therefrom, the above steps may be executed in any order or in parallel. Hence, it is to be appreciated that the present invention is not be limited to the above-described order of steps.

Figure 3:
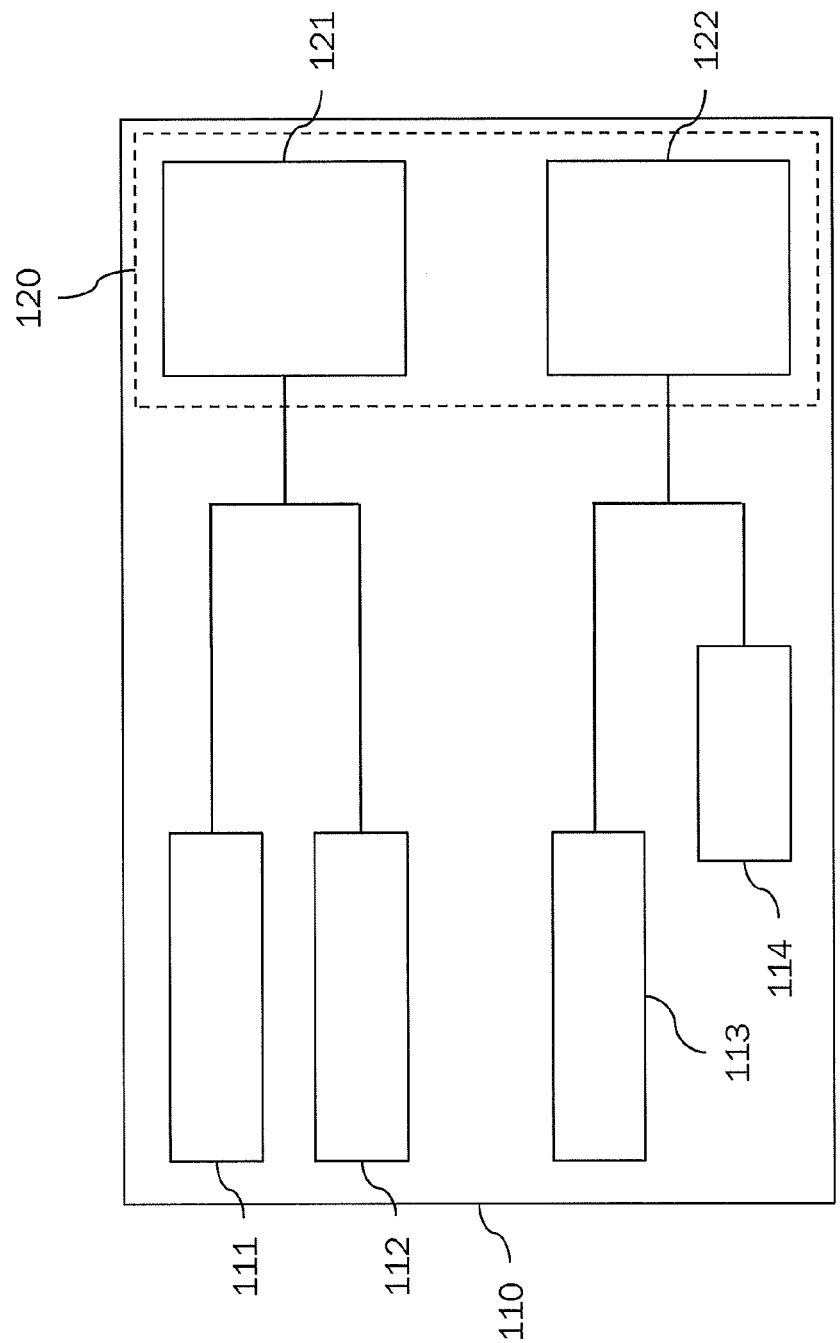
FIG. 3 is a schematic view of the detecting means and the measuring circuitry comprised by the mobile unit.

With reference to FIG. 3, now an implementation of the first detecting means 110 will be described. It is to be noted that the described implementation also applies to the third detecting means 260 which is of the same type as the first detecting means 110.

In a preferred embodiment, the first detecting means 110 comprises a first detecting device 111, a second detecting device 112, and a third detecting device 113. The first detecting means 110 may further comprise a fourth detecting device 114.

The first detecting means 110 further comprises the first measuring circuitry 120. The first measuring circuitry 120 includes first measuring sub-circuitry 121 connected to the first and second detecting devices 111, 112 and second measuring sub-circuitry 122 connected to the third detecting device 113 and, if present, the fourth detecting device 114. The first measuring circuitry 120 is connected to the first processing unit 130. In addition, the first through third measuring devices 111, 112, 113 and the fourth detecting device 114 may be connected to the first processing unit 130 directly.

The first detecting device 111 is configured for detecting a first variable (first energy variable) related to an ionizing particle incident on the first detecting device 111 if the first variable is in a first range.

One case of the first variable is a deposited energy. That is, the first detecting device 111 is configured for detecting a first energy that is deposited in the first detecting device 111 by an ionizing particle incident on the first detecting device 111 if the deposited energy is in a first energy range. In other words, the first detecting device 111 is configured for detecting an energy deposited by an ionizing particle in the first detecting device 111 in the first energy range.

The second detecting device 112 is configured for detecting a second variable (second energy variable) related to an ionizing particle incident on the second detecting device 112 if the second variable is in a second range.

One case of the second variable is a deposited energy. That is, the second detecting device 112 is configured for detecting a second energy that is deposited in the second detecting device 112 by an ionizing particle incident on the second detecting device 112 if the deposited energy is in a second energy range. In other words, the second detecting device 112 is configured for detecting an energy deposited by an ionizing particle in the second detecting device 112 in the second energy range.

In a specific implementation of the present invention, the first detecting device 111 includes a first silicon diode (thick diode) having a sensitive area of 0.25 $cm^2$ and a sensitive depth of 300 μm, wherein the thickness of the dead layer is less than 1 μm. The second detecting device 112 includes a second silicon diode (thin diode) having a sensitive area of 0.25 $cm^2$ and a sensitive depth of 7 μm, wherein the thickness of the dead layer is less than 1 μm. The silicon diodes may be provided with converters for converting neutrons into particles that may be detected by the silicon diodes, such as neutron converter foils covering the silicon diodes. Such neutron converter foils are disclosed in patent application WO 03/007018 A2), which is hereby incorporated by reference.

The thick and thin diodes each measure energy deposited by ionizing particles in silicon. The respective energies deposited in silicon are read out by respective read-out electronics from the thick and thin diodes, and converted to an energy deposited in water, thereby obtaining an absorbed dose in units of Gray (Gy). Therein, the responses of the diodes are derived from first principles, a set of simulations and assumptions about the physical dimensions of the sensitive volumes. By the thick diode, pulse heights of energy deposition in the first range (first energy range) between 50 keV and 15 MeV can be detected. By the thin diode, pulse heights of energy deposition in the second range (second energy range) between 200 keV and 25 MeV can be detected.

Having knowledge of the medium path length of ionizing particles passing through the thick and thin diode, not only absorbed doses, but also linear energy deposition spectra (spectra of linear energy transfers in water) can be obtained for the thick and thin diode, respectively. Therein, the medium path length is directly proportional to the effective thickness of the respective diode. Using the thick diode, a LET in water in a range from 0.08 keV/μm to 25 keV/μm can be detected, whereas using the thin diode a LET in water in a range from 10 keV/μm to 1800 keV/μm can be detected.

In the above, a combined range (combined energy range) obtained by combining the first and second energy ranges consists of a first sub-range in which energy deposition by ionizing particles can be detected by the first detecting device 111 only (i.e. that is covered by the first detecting device 111 only), a second sub-range in which energy deposition by ionizing particles can be detected by the second detecting device 112 only (i.e. that is covered by the second detecting device 112 only), and a third sub-range in which energy deposition by ionizing particles can be detected by both the first and second detecting devices 111, 112 (i.e. that is covered by both the first and second detecting devices 111, 112). However, it has to be noted that a particle of a given energy would deposit different amounts of energy in the first and second detecting devices 111, 112, which is due to the different thickness of the diodes.

When considering the LET as the second case of the first and second variables, the above-mentioned differences resulting from different thickness of the diodes are no longer present. The first and second detecting devices are configured so that also for the LET in water, there is a first LET sub-range in which a LET can only be detected by the first detecting device 111 (i.e. that is covered by the first detecting device 111 only), a second LET sub-range in which the LET can only be detected by the second detecting device 112 (i.e. that is covered by the second detecting device 112 only), and a third LET sub-range in which the LET can be detected by both the first and second detecting devices 111, 112 (i.e. that is covered by both the first and second detecting devices 111, 112). According to the above configuration of the first and second detecting devices 111, 112, a LET in water can be detected by only the first detecting device 111 in the first LET sub-range (0.08 keV/μm, 10 keV/μm), by only the second detecting device 112 in the second LET sub-range (25 keV/μm, 1800 keV/μm) and by both the first and second detecting devices 111, 112 in the third LET sub-range (10 keV/μm, 25 keV/μm), wherein a combined range of detectable LET in water is (0.08 keV/μm, 1800 keV/μm). Herein, (a, b) is understood to denote a range from a to b, and 1 eV corresponds to approximately $1.6 \cdot 10^{-19}$ J (Joules).

The first and second detecting devices 111, 112 are identical except for the fact that the first detecting device 111 comprises the thick diode, and the second detecting device 112 comprises the thin diode, wherein however operational parameters may be different. Therefore, as far as components apart from the thick diode are concerned, the following more detailed description of the first detecting device 111 also applies to the second detecting device 112.

In addition to the thick diode, the first detecting device 111 includes a charge-sensitive pre-amplifier, a shaping amplifier, and an A/D-converter. The thick diode is reverse-biased for operation. The bias voltage is chosen so that the whole thickness of the thick diode (300 μm) is fully depleted. The same holds true for the thin diode of the second detecting device 112, wherein however the bias voltage in the thin diode is lower than the bias voltage in the thick diode.

The ionization potential $E_I$ in silicon is 3.62 eV (at room temperature). If an ionizing particle deposits energy in the respective diode, electron-hole pairs are created, wherein the number of pairs depends on the energy deposited by the ionizing particle. In more detail, the number N of electron-hole pairs corresponds to the deposited energy $E_D$ divided by the ionization potential $E_I$, $N=E_D/E_I$. A charge proportional to the number of electron-hole pairs is input to the charge-sensitive pre-amplifier which outputs a voltage step proportional to the total charge. The output of the charge-sensitive pre-amplifier is fed to the shaping amplifier which is formed by a second-order band-pass filter and suppresses noise. The output of the shaping amplifier represents the energy deposited by the respective particle in the diode. By means of the A/D-converter, the output of the shaping amplifier is converted into a digital signal suitable for processing by the first measuring circuitry 120 or the processing unit 130 of the mobile unit 100.

Combining the data that is output by the thick and thin diode enables to determine the full LET transfer spectrum in the range (0.08 keV/μm, 1800 keV/μm). On the basis of the full LET transfer spectrum, the dose equivalent (dose equivalent) in unit of Sievert (Sv) can be determined by weighing the full LET transfer spectrum with a LET-dependent quality factor (i.e. by convoluting the full LET spectrum with the quality factor). Therefore, the combination of the data output by the thick and the thin diodes (i.e. by the first and second detecting devices 111, 112) enables to determine the absorbed dose, the LET spectrum and the dose equivalent in unknown radiation fields with optimum accuracy.

The third detecting device 113 is configured for detecting a third variable (third energy variable) related to an ionizing particle incident on the third detecting device 113 if the third variable is in a third range.

One case of the third variable is a deposited energy. That is, the third detecting device 113 is configured for detecting a third energy that is deposited in the third detecting device 113 by an ionizing particle incident on the third detecting device 113 if the deposited energy is in a third energy range. In other words, the third detecting device 113 is configured for detecting an energy deposited by an ionizing particle in the third detecting device 113 in the third energy range.

In the specific implementation of the present invention, the third detecting device 113 includes a reaction chamber (ionization chamber) based on direct ion storage (DIS) technology. The ionization chamber is filled with nitrogen gas at a pressure of about 90 to 95 kPa and has a volume of about 60 $mm^3$. The ionization chamber is surrounded by conductive liquid crystal polymer (LCP) plastics, for example with about 20% carbon loading. The third detecting device 113 allows determining an absorbed dose.

Operation of the third detecting device 113 is analogous to the operation of the TEPC. However, instead of a positively biased anode wire, the ionization chamber includes a collection wire that is biased according to a collecting voltage polarity switch mode, that is, polarity of the wire is periodically reversed. Depending on the bias of the collecting wire, positively charged ions or negatively charged electrons drift towards the collecting wire. Therein, the period with which the polarity is reversed is chosen longer than a maximum drift time in the ionization chamber. By periodically reversing the polarity of the collecting wire, the third detecting device 113 can be operated continuously, even if no ground is available for grounding the collecting wire.

In the above, the combined energy range obtained by combining the first and second energy ranges is fully contained in the third energy range. Thus, the third detecting device 113 offers a baseline comparison of the output obtained by combining the data from the first and second detecting devices 111, 112, so that e.g. a calibration of the first and second detecting devices 111, 112 can be checked on-line, or aging effects of the first and second detecting devices 111, 112 can be recognized on-line and be corrected for.

The first detecting means 110, more precisely the first measuring circuitry 120, is configured to obtain the first quantity on the basis of an output of the first and second detecting devices 111, 112, or preferably on the basis of an output of the first, second and third detecting devices 111, 112, 113. In the former case, LET spectra for both the first and second detecting devices 111, 112 are obtained by taking into account the respective medium path lengths of the thick and thin diodes. Since at the level of LET spectra, the different thicknesses of the thick and thin diodes have been accounted for, the LET spectra for the first and second detecting devices 111, 112 can be combined into a combined LET spectrum. Thereby, a wider range for the LET spectrum, i.e. (0.08 keV/µm, 1800 keV/µm) in the present example, can be covered than would be possible with a single detecting device. The dose equivalent, as the first quantity is then obtained from the combined LET spectrum by measures known to the expert skilled in the art. These measures involve convoluting the combined LET spectrum with a particle number per unit LET and multiplying the result by a conversion factor of $1.6 \cdot 10^{-19}$ J/eV.

In the latter case, if the first quantity is obtained on the basis of an output of the first, second and third detecting devices 111, 112, 113, an absorbed dose is determined by commonly known measures from the combined LET spectrum, which is obtained as in the above case. This absorbed dose is compared to the absorbed dose output by the third detecting device 113. On the basis of the comparison, it is decided whether it is proceeded with the combined LET spectrum, or whether a warning message indicating a deviation between the respective absorbed doses is to be issued. If a deviation between the respective absorbed doses is within a predetermined margin for the absorbed doses, it is proceeded with the combined LET spectrum, and the dose equivalent is obtained from the combined LET spectrum as in the above case. It is understood that in addition to issuing the warning message also the first quantity may be obtained and output.

Thus, as described above, the first quantity (equivalent dose) is obtained on the basis of the combination of data output by the first and second detecting devices 111, 112. In more detail, preferably, the first quantity is obtained on the basis of data output by the first, second and third detecting devices 111, 112, 113.

A detecting device that may be employed as the third detecting device 113 is disclosed in patent application WO 95/12134 A1 which is hereby incorporated by reference.

The fourth detecting device 114 is configured for detecting a time-integrated value of a fourth variable (fourth energy variable) related to an ionizing particle incident on the fourth detecting device 114. A preferred case of the fourth variable is a total energy. In this case, the fourth detecting device 114 is configured for detecting a total energy that is deposited in the fourth detecting device 114 by ionizing particles incident on the fourth detecting device 114 over time.

According to a specific implementation of the present invention, the fourth detecting device 114 includes a radiation sensing field effect transistor (RADFET) measuring an absorbed dose in silicon. The RADFET is a p-type MOSFET that collects to its gate region a part of the charge generated in the oxide by ionizing particles. When the RADFET is exposed to ionizing radiation, electron-hole pairs are generated in its silicon oxide layer. The holes move slowly towards the silicon substrate. Because of the well-known nature of $SiO_2$, hole traps exist as an intrinsic part of the oxide, wherein the density of hole traps is greater near the $Si/SiO_2$ interface. As the holes move towards the silicon substrate, a certain number of the holes get trapped, and accordingly the positive charge within the oxide and at the $Si/SiO_2$ interface increases as a function of absorbed dose.

As the positive charge in the bulk of the oxide and at the interface increases, the RADFET becomes harder to switch on, i.e. its absolute threshold voltage becomes larger. By this change in threshold voltage, the absorbed dose can be determined.

The RADFET is configured as follows: source and bulk terminals are connected, and also gate and drain terminals are connected. When the RADFET is not being read out, all four terminals are grounded. To read out the RADFET, a constant current is applied to the gate terminal (and the drain terminal), and a DC voltage is read out at the gate terminal (or the drain terminal). A difference between the read-out DC voltage and a reference voltage that corresponds to the un-irradiated (i.e. factory-new) RADFET is proportional to the absorbed dose.

As described above, the RADFET is operated as a passive detector, which means that there is no physical method to remove the dose signal from the detector as soon as it has been stored as an accumulated charge in the FET oxide. This adds reliability to the detector since there is no way to lose any significant dose from the RADFET, and the RADFET can be read out and analyzed even after all other detectors would have failed (see below).

The RADFET (i.e. the fourth detecting device 114) has a detection threshold for an absorbed dose that is larger than a detection threshold for an absorbed dose of any of the first through third detecting devices 111, 112, 113. Preferably, the detection threshold of the RADFET is by about a factor of 1000 larger than the detection threshold of the third detecting device 113 (e.g. 10 mGy for the RADFET compared to 10 pGy for the third detecting device 113), wherein the detection thresholds of the first through third detecting devices 111, 112, 113 are substantially equal. As is exemplified by the discrepancy in detection thresholds, the RADFET is specifically adapted to determine an absorbed dose resulting from very high dose events that could not be determined by means of any of the first through third detecting devices 111, 112, 113. Thus, the fourth detecting device 114 serves as a warning system that is capable of providing a quantitative assessment of an absorbed dose even in cases in which the other detecting devices would fail due to excessively high levels of radiation.

If the first detecting means 110 comprises also the fourth detecting device 114, the first detecting means 110, more precisely the measuring circuitry 120, may be configured to obtain the first quantity on the basis of an output of the first through fourth detecting devices 111, 112, 113, 114. As described above, a dose equivalent is determined on the basis of the output of the first and second detecting devices 111, 112, or preferably, on the basis of the output of the first through third detecting devices 111, 112, 113. However, if an absorbed dose above the detection threshold of the fourth detecting device 114 is detected by the fourth detecting device 114, it is concluded that a high dose event corresponding to a burst of radiation has taken place. In this case, the absorbed dose detected by the fourth detecting means is output as the first quantity.

In alternative embodiments, the first detecting means 110 may comprise any, any two, any three or all of the detecting devices described above.

As indicated above, the digital electronics of the mobile unit 100 is normally in a sleep mode for reasons of energy conservation, and is woken up with a short response time upon particle detection in the first detecting means 110 so that each particle hitting the first detecting means 110 is detected and accounted for. In more detail, the firmware architecture of the mobile unit 100 is interrupt-controlled, wherein the interrupt may relate to an internal interrupt, such as a timer signal, or an external interrupt, such as detection of a particle in the first detecting means 110. Therein, the first and second detecting devices 111, 112 (diodes) act as monitor detecting devices. That is, if a particle hits either of the diodes, energy deposition by the particle in the respective diode will be detected by the analog electronics of the first detecting means 110. Alternatively, also the third detecting device 113 could act as the monitor detecting device. Detection of energy deposition by the analog electronics serves as a trigger (seed signal) for waking up the digital electronics of the mobile unit 100 including the processing unit 130, wherein the processing unit 130 can wake up from sleep within microseconds. This time interval is short enough to avoid missing any radiation events because of the digital electronics of the mobile unit 100 being in the sleep mode. Since the diodes cover a range for energy deposition from 50 keV to 25 MeV and for linear energy transfers (LET) from 0.08 keV/μm to 1800 keV/μm, it is also ensured that no radiation event within the energy range relevant for personal dosimetry is missed. In particular, a case in which rare, yet very high energy particles that can account for a good part of an acceptable dose equivalent are lost, is avoided by the above configuration.

Figure 4:
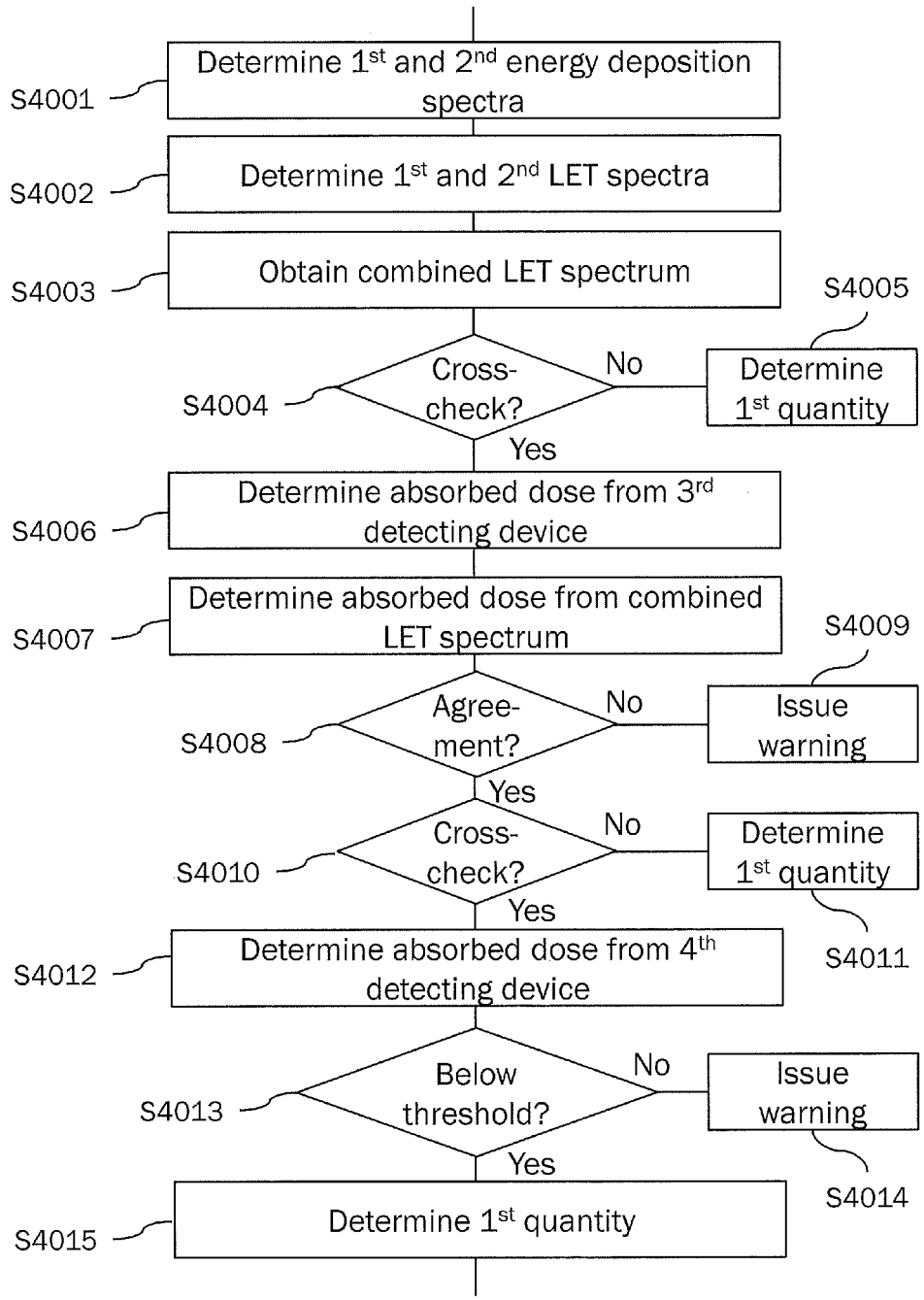
FIG. 4 is a flow chart illustrating operation of the detecting means comprised by the mobile unit.

Next, with reference to the flow chart of FIG. 4, determination of the first quantity by the first detecting means 110 will be described. It is understood that the quantities referred to below relate to an equal period of time, preferably the predetermined period of time.

At step S4001, a first energy deposition spectrum of energy deposited in the first detecting device 111 (quantity indicative of a spectrum of energy deposition in the first detecting device 111) and a second energy deposition of energy deposited in the second detecting device 112 (quantity indicative of a spectrum of energy deposition in the second detecting device 112) are determined.

At step S4002, a first LET spectrum (quantity indicative of a spectrum of energy transfer per unit path length in the first detecting device 111) is obtained from the first energy deposition spectrum, taking into account the medium path length in the first detecting device 111. Further, a second LET spectrum (quantity indicative of a spectrum of energy transfer per unit path length in the second detecting device 112) is obtained from the second energy deposition spectrum, taking into account the medium path length in the second detecting device 112.

At step S4003, the first and second LET spectra are combined to obtain a combined LET spectrum (quantity indicative of a spectrum of energy transfer per unit path length in the first detecting device 111 and the second detecting device 112).

At step S4004, it is decided whether plausibility of the outputs of the first and second detecting devices 111, 112 is to be cross-checked against an output of the third detecting device 113. If it is envisaged to perform the cross-check, operation proceeds with step S4006, otherwise with step S4005. In a preferred embodiment, the cross-check is envisaged.

At step S4005, if the cross-check is not envisaged, the dose equivalent is obtained from the combined LET spectrum by measures described above and well known to the expert skilled in the art and output as the first quantity.

At step S4006, if the cross-check is envisaged, an absorbed dose in the third detecting device 113 (quantity indicative of an absorbed dose in the third detecting device 113) is obtained from the third detecting device 113, and at step S4007, an absorbed dose in the first and second detecting devices 111, 112 (quantity indicative of an absorbed dose in the first and second detecting devices 111, 112) is obtained from the combined LET spectrum by measures described above well known to the expert skilled in the art.

At step S4008, it is checked whether or not the absorbed dose in the third detecting device 113 agrees with the absorbed dose in the first and second detecting devices 111, 112. If agreement within a predetermined margin is found, operation proceeds with step S4010, otherwise with step S4009.

At step S4009, if agreement within the predetermined margin is not found, a warning message indicating the non-agreement is issued. In addition, the dose equivalent may be nevertheless obtained from the combined LET spectrum and output as the first quantity.

At step S4010, if agreement within the predetermined margin is found, it is decided whether the absorbed dose in the first and second detecting devices 111, 112 is to be cross-checked against an output of the fourth detecting device 114. If it is envisaged to perform the cross-check, operation proceeds with step S4012, otherwise with step S4011. In a further preferred embodiment, the cross-check is envisaged.

At step S4011, if the cross-check is not envisaged, the dose equivalent is obtained from the combined LET spectrum by measures described above and well known to the expert skilled in the art and output as the first quantity, similarly to step S4005.

At step S4012, if the cross-check is envisaged, an absorbed dose in the fourth detecting device 114 (quantity indicative of an absorbed dose in the fourth detecting device 114) is obtained from the fourth detecting device 114.

At step S4013, it is checked whether or not the absorbed dose in the fourth detecting device 114 is below a predetermined threshold for the absorbed dose in the fourth detecting device 114. If the absorbed dose in the fourth detecting device 114 is below the predetermined threshold, operation proceeds with step S4015, otherwise with step S4014.

At step S4014, if the absorbed dose in the fourth detecting device 114 is not below the predetermined threshold, a warning message indicating a high dose event is issued. Additionally, the absorbed dose in the fourth detecting device 114 may be output as the first quantity.

At step S4015, if the absorbed dose in the fourth detecting device 114 is below the predetermined threshold, the dose equivalent is obtained from the combined LET spectrum by measures described above and well known to the expert skilled in the art and output as the first quantity, similarly to steps S4005 and S4011.

Figure 5:
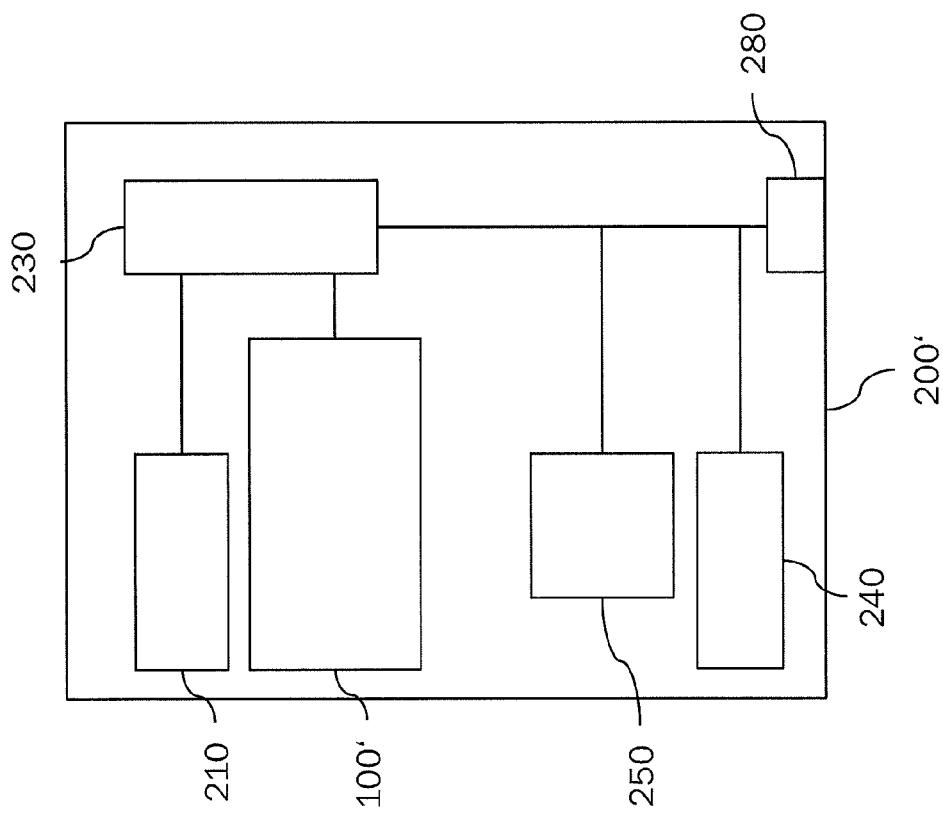
FIG. 5 is a schematic view of the main unit according to a further embodiment of the invention.

Next, with reference to FIG. 5, an advantageous implementation of the main unit 200' will be described.

According to this advantageous implementation, instead of the third detecting means 260, the main unit 200' comprises a second (or fixed) mobile unit 100' (second first unit or further first unit) which is identical in configuration to the mobile unit 100 described above. The third quantity is output by the second mobile unit 100'. Otherwise, the main unit 200' is identical to the main unit 200 described above with reference to FIG. 1.

By providing the fixed mobile unit 100' within the main unit 200', systematic errors that may affect the determination of the quantity for adjusting the first quantity can be excluded to an even higher degree, since now also identical read-out and processing electronics are provided in connection with the first quantity and the third quantity.

In addition to determining the quantity for adjusting the first quantity, the fixed mobile unit 100' may also be employed to determine adjusted calibration coefficients for the mobile unit 100 and any possible additional mobile units. Accordingly, a LET spectrum (corresponding to a predetermined period of time) output by the fixed mobile unit 100' may be compared to a LET spectrum (corresponding to the predetermined period of time) output by the second detecting means 210. If a deviation between the respective LET spectra is observed, calibration coefficients of the fixed mobile unit 100' (more precisely, calibration coefficients of a first detecting means of the fixed mobile unit) are adjusted according to a predetermined scheme. If e.g. if a shift in the LETs of the respective spectra is observed, calibration coefficients of the fixed mobile unit 100' are adjusted to remove the observed shift. The comparison of spectra and the adjusting of calibration coefficients may be performed iteratively. Once adjusted calibration coefficients of the fixed mobile unit 100' are determined so that the LET spectrum output by the fixed mobile unit 100' reproduces the LET spectrum output by the second detecting means 210, the adjusted calibration coefficients of the fixed mobile unit 100' are transmitted to the mobile unit 100 and the possible additional mobile units, in which the respective processing unit 130 replaces the previous calibration coefficients with the adjusted calibration coefficients. Thereby, on-line calibration of the mobile unit 100 can be achieved. Of course, such adjustment of calibration coefficients and on-line calibration of the mobile unit 100 is also possible if the main unit includes the third detecting means 260.

The main unit 200 may be a knowledge-based system, in the sense that e.g. optimum calibration coefficients or other operation parameters both of the main unit 200 and the mobile unit 100, 100' are adjusted on the basis of previously acquired data, for instance data acquired earlier during the current operation or during previous operations.

Figure 6:
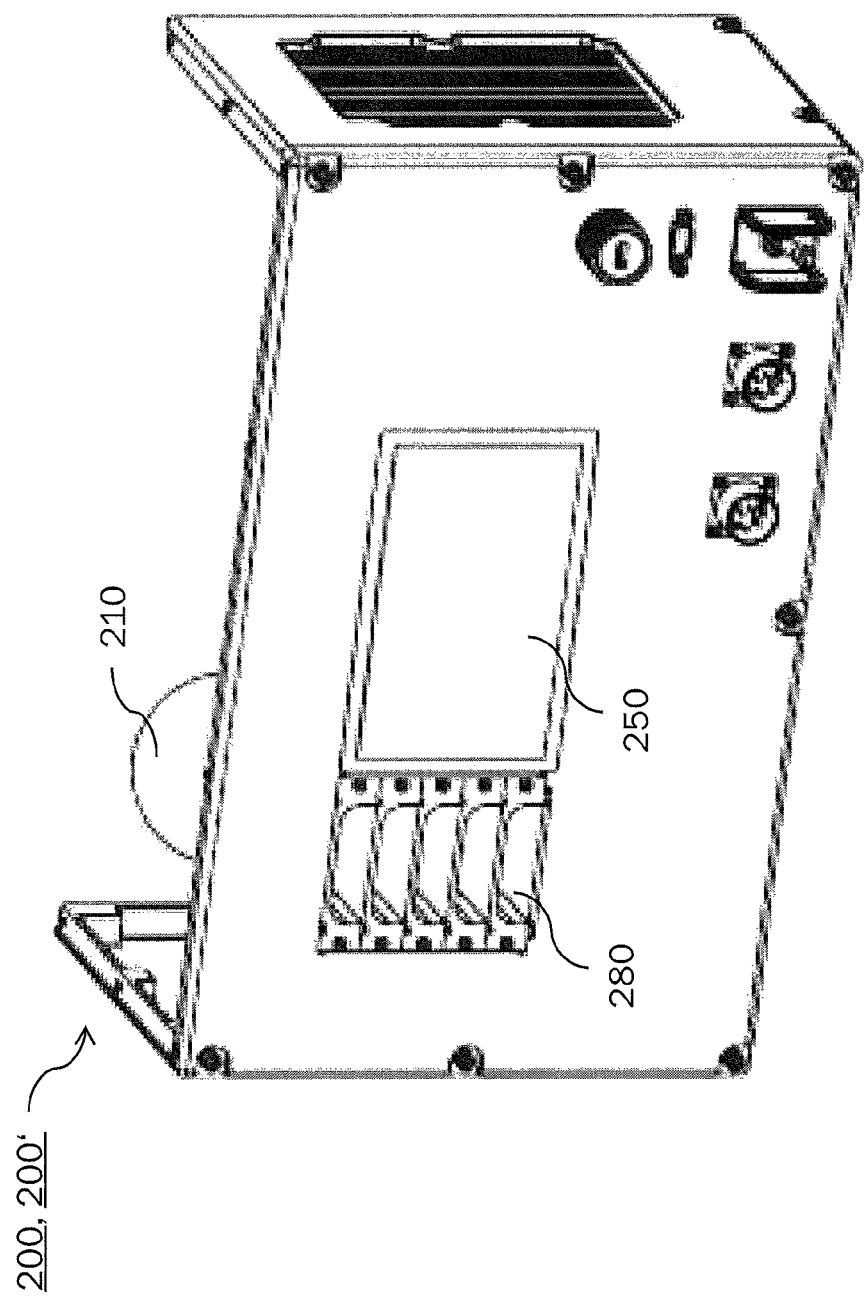
FIG. 6 is a view of the front of the main unit according to the present invention.

FIG. 6 shows a front view of the main unit 200, wherein a rear cover of the main unit 200 has been removed. In FIG. 6, the second detecting means 210, the output device 250 and five mounting means 280 for receiving mobile units 100 can be seen.

Figure 7:
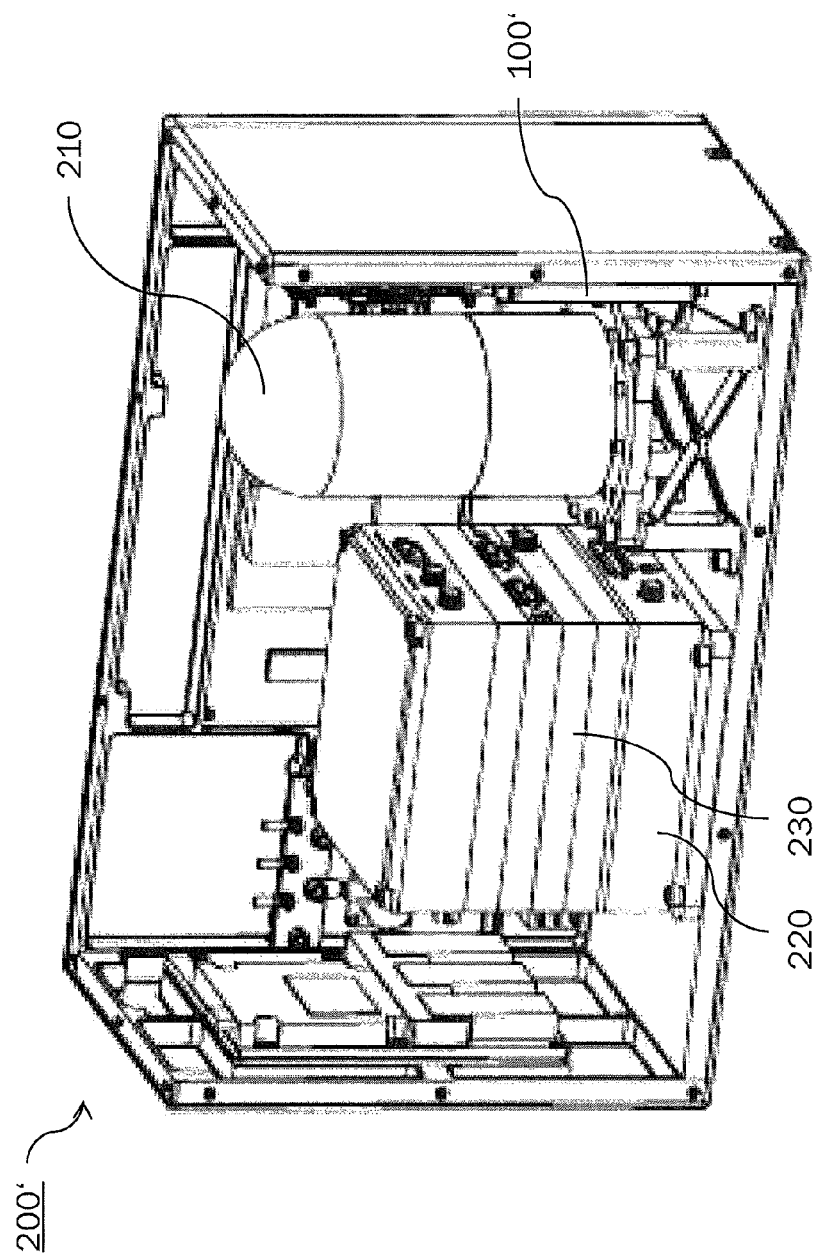
FIG. 7 is a view of the back of the main unit according to the present invention.

FIG. 7 shows a rear view of the main unit 200, wherein the rear cover of the main unit 200 has been removed. In FIG. 7, the second detecting means 210, the second measuring circuitry 220 and the processing unit 230 can be seen.

It is noted that in addition to medical monitoring, the inventive dosimeter system and the inventive mobile dosimeter unit are also applicable to detecting radiation smuggling. If radioactive material is moved in proximity of the mobile unit 100 or the main unit 200, this results in a time-variable radiation pattern that is detected by the detecting means included in the mobile unit 100 or the main unit 200, respectively. Thereby, illicit transportation of radioactive material can be detected by the inventive dosimeter system or the inventive mobile dosimeter unit e.g. by employing same at baggage screening or at security gates at airports.

Features, components and specific details of the structures of the above-described embodiments may be exchanged or combined to form further embodiments optimized for the respective application. As far as those modifications are readily apparent for an expert skilled in the art, they shall be disclosed implicitly by the above description without specifying explicitly every possible combination, for the sake of conciseness of the present description.

What is claimed is:

1. A dosimeter system for determining radiation exposure comprising a first unit and a second unit,
    wherein the first unit comprises:
    first detecting means configured for determining a first quantity indicative of an influence of a first radiation field; and
    transmitting means for transmitting the first quantity determined by the first detecting means to the second unit;
    wherein the second unit comprises:
    second detecting means configured for determining a second quantity indicative of an influence of a second radiation field on biological tissue;
    third detecting means configured for determining a third quantity indicative of an influence of the second radiation field, wherein the third detecting means is of the same type as the first detecting means comprised by the first unit; and
    means for determining a quantity for adjusting the first quantity on the basis of the second quantity determined by the second detecting means and the third quantity determined by the third detecting means, wherein the quantity for adjusting the first quantity is determined such that a fourth quantity indicative of an influence of the first radiation field on biological tissue can be determined on the basis of the first quantity determined by the first detecting means and the quantity for adjusting the first quantity.

2. The dosimeter system according to claim 1, wherein the second unit further comprises means for determining the fourth quantity indicative of an influence of the first radiation field on biological tissue on the basis of the first quantity determined by the first detecting means and the quantity for adjusting the first quantity.

3. The dosimeter system according to claim 1, wherein the first quantity is a quantity indicative of an influence of the first radiation field on biological tissue and the third quantity is a quantity indicative of an influence of the second radiation field on biological tissue.

4. The dosimeter system according to claim 1, wherein the first quantity is a dose equivalent and the third quantity is a dose equivalent.

5. The dosimeter system according to claim 1,
wherein the first unit further comprises means for determining a position of the first unit;
the transmitting means is configured to transmit the first quantity determined by the first detecting means and the determined position of the first unit to the second unit; and
the second unit comprises means for determining a function indicative of an intensity of the first radiation field in dependence on the position of the first on the basis of the first quantity and the determined position of the first unit.

6. The dosimeter system according to claim 5,
wherein the system comprises a plurality of first; and
the second unit comprises means for determining a spatial distribution of the first radiation field in which the plurality of first units are present on the basis of the respective functions indicative of the intensity of the first radiation field in dependence on the position of the respective first unit.

7. The dosimeter system according to claim 1,
wherein the first detecting means comprises a first detecting device configured for detecting a first variable related to an ionizing particle incident on the first detecting; and
the first detecting device has a first range in which the first variable can be detected.

8. The dosimeter system according to claim 7,
wherein the first detecting means further comprises a second detecting device configured for detecting a second variable related to an ionizing particle incident on the second detecting device;
the second detecting device a second range in which the second variable can be detected; and
the first detecting means is configured to obtain the first quantity on the basis of an output of the first and second detecting devices.

9. The dosimeter system according to claim 8,
wherein the first and second detecting devices are configured so that a range obtained by combining the first and second ranges consists of a first sub-range covered by the first detecting device only, a second sub-range covered by the second detecting device only, and a third sub-range covered by both the first and second detecting devices.

10. The dosimeter system according to claim 8,
wherein the first detecting means further comprises a third detecting device configured for detecting a third variable related to an ionizing particle incident on the third detecting device;
the third detecting device a third range in which the third variable can be detected;
a range obtained by combining the first and second ranges is fully contained in the third range; and
the first detecting means is configured to obtain the first quantity on the basis of an output of the first, second and third detecting devices.

11. The dosimeter system according to claim 10, wherein the first variable, the second variable and the third variable are a deposited energy or a linear energy transfer.

12. The dosimeter system according to claim 1, wherein the first detecting means comprises a fourth detecting device configured for detecting a time-integrated value of a fourth variable related to an ionizing particle incident on the fourth detecting device.

13. The dosimeter system according to claim 12, wherein the fourth variable is an energy deposited in the fourth detecting device, and the fourth detecting device is configured for detecting a total energy that is deposited in the fourth detecting device by ionizing particles over time.

14. The dosimeter system according to claim 1, wherein the first unit comprises
a shock detector configured for detecting a mechanic shock of the first unit; and
means for correcting the first quantity determined by the first detecting means for an influence of the mechanic shock of the first unit detected by the shock detector.

15. The dosimeter system according to claim 1, wherein the second unit comprises mounting means configured for receiving the first unit in the mounting means, for charging a battery of the first unit and for read or write operations to or from a memory of the first unit.

16. A method for determining radiation exposure, comprising:
determining a first quantity indicative of an influence of a first radiation field by a first detecting
determining a second quantity indicative of an influence of a second radiation field on biological tissue by a second detecting means;
determining a third quantity indicative of an influence of the second radiation field by a third detecting means, wherein the third detecting means is of the same type as the first detecting means;
determining a quantity for adjusting the first quantity on the basis of the second quantity determined by the second detecting means and the third quantity determined by the third detecting means; and
determining a fourth quantity indicative of an influence of the first radiation field on biological tissue on the basis of the first quantity determined by the first detecting means and the quantity for adjusting the first quantity.

* * * * *